United States Patent
Wang et al.

(10) Patent No.: US 11,766,324 B2
(45) Date of Patent: Sep. 26, 2023

(54) INTRAOCULAR LENS AND MANUFACTURING METHOD THEREFOR

(71) Applicant: EYEBRIGHT MEDICAL TECHNOLOGY (BEIJING) CO., LTD., Beijing (CN)

(72) Inventors: Zhao Wang, Beijing (CN); Shuyan Guo, Beijing (CN); Jiangbing Xie, Beijing (CN)

(73) Assignee: EYEBRIGHT MEDICAL TECHNOLOGY (BEIJING) CO., LTD., Beijing (CN)

(*) Notice: Subject to any disclaimer, the term of this patent is extended or adjusted under 35 U.S.C. 154(b) by 320 days.

(21) Appl. No.: 17/258,374

(22) PCT Filed: Jul. 12, 2019

(86) PCT No.: PCT/CN2019/095785
§ 371 (c)(1),
(2) Date: Jan. 6, 2021

(87) PCT Pub. No.: WO2020/011250
PCT Pub. Date: Jan. 16, 2020

(65) Prior Publication Data
US 2021/0267754 A1    Sep. 2, 2021

(30) Foreign Application Priority Data

Jul. 13, 2018   (CN) .......................... 201810769524.5
Jul. 13, 2018   (CN) .......................... 201821112563.X
(Continued)

(51) Int. Cl.
*A61F 2/16*   (2006.01)
(52) U.S. Cl.
CPC ................................ *A61F 2/1618* (2013.01)

(58) Field of Classification Search
None
See application file for complete search history.

(56) References Cited

U.S. PATENT DOCUMENTS 5,114,220 A    5/1992  Baude et al.
5,699,142 A   12/1997  Lee et al.
(Continued)

FOREIGN PATENT DOCUMENTS

AU           622420 B2    4/1992
AU      2018204425 A1    7/2018
(Continued)

OTHER PUBLICATIONS

Bernal-Molina Paula et al: "Depth-of-Field of the Accommodating Eye", Optometry and Vision Science, vol. 91, No. 10, Oct. 1, 2014 (Oct. 1, 2014), pp. 1208-1214, XP055868427, US, ISSN: 1040-5488, DOI: 10.1097/OPX.0000000000000365, Retrieved from the Internet: URL:https://www.ncbi.nlm.nih.gov/pmc/articles/PMC4461356/pdf/opx-91-1208.pdf>.

*Primary Examiner* — Javier G Blanco
(74) *Attorney, Agent, or Firm* — The Ollila Law Group LLC

(57) ABSTRACT

The present invention relates to an aspherical multifocal intraocular lens with large depth of field, the intraocular lens having an anterior optical surface and a posterior optical surface, wherein one optical surface is distributed with an aspherical surface which plays a role of expanding the depth of field, and the other optical surface is distributed with a multifocal structure which plays a role of providing two or more focal points. The aspherical surface provides a depth of field matching with an absolute value of a difference in refractive power of at least one pair of adjacent focal points of the two or more focal points provided by the multifocal structure. The aspherical surface, on the one hand, allows a continuous visual range between the focal points and, on the (Continued)

other hand, extends near vision in the direction of near focal point through the depth of field, thereby enabling continuous, uninterrupted full-range vision and adequate near vision. The present invention also relates to a method for manufacturing an intraocular lens. The present invention also relates to an artificial lens, and more particularly to an artificial lens that makes use of excessive resolution to achieve focal extension. The present invention also relates to a method for manufacturing an artificial lens.

27 Claims, 12 Drawing Sheets

(30) Foreign Application Priority Data

Sep. 5, 2018 (CN) .......................... 201811032706.0
Sep. 5, 2018 (CN) .......................... 201821448242.7

(56) References Cited

U.S. PATENT DOCUMENTS

| | | |
|---|---|---|
| 6,406,494 B1 | 6/2002 | Laguette et al. |
| 8,240,850 B2 | 8/2012 | Apter et al. |
| 8,747,466 B2 | 6/2014 | Weeber et al. |
| 2003/0225455 A1 | 12/2003 | Cathey, Jr. |
| 2006/0098163 A1 | 5/2006 | Bandhauer et al. |
| 2009/0147378 A1 | 6/2009 | Zalevsky et al. |
| 2009/0187242 A1 | 7/2009 | Weeber et al. |
| 2010/0016962 A1 | 1/2010 | Hong et al. |
| 2010/0234943 A1* | 9/2010 | Portney ................. A61F 2/1618 623/6.23 |
| 2014/0084501 A1 | 3/2014 | Bille |
| 2014/0358225 A1* | 12/2014 | Wang .................... A61F 2/1613 623/6.27 |
| 2016/0193037 A1 | 7/2016 | Pinto et al. |
| 2017/0245987 A1 | 8/2017 | Canovas Vidal et al. |

FOREIGN PATENT DOCUMENTS

| | | | |
|---|---|---|---|
| CA | 2642019 A1 | | 8/2007 |
| CA | 2675256 A1 | | 7/2008 |
| CN | 1039487 A | | 2/1990 |
| CN | 101416097 A | | 4/2009 |
| CN | 101677852 A | | 3/2010 |
| CN | 102438549 A | | 5/2012 |
| CN | 104490490 A | | 4/2015 |
| CN | 104755012 A | | 7/2015 |
| CN | 104783925 A | | 7/2015 |
| CN | 104783925 A | * | 7/2015 |
| CN | 204964917 U | | 1/2016 |
| CN | 106291976 A | | 1/2017 |
| CN | 106353892 A | | 1/2017 |
| CN | 107072779 A | | 8/2017 |
| CN | 107212949 A | | 9/2017 |
| CN | 108066046 A | | 5/2018 |
| CN | 108078654 A | | 5/2018 |
| CN | 108836571 A | | 11/2018 |
| CN | 109009567 A | | 12/2018 |
| EP | 3461460 A1 | | 4/2019 |
| EP | 3470019 A1 | | 4/2019 |
| WO | 2006060477 A2 | | 6/2006 |
| WO | 2009027438 A2 | | 3/2009 |
| WO | 2016040331 A1 | | 3/2016 |
| WO | 2016111851 A1 | | 7/2016 |
| WO | 2017213232 A1 | | 12/2017 |

* cited by examiner

INTRAOCULAR LENS AND MANUFACTURING METHOD THEREFOR

FIELD OF THE INVENTION

The present invention relates to an intraocular lens and a method for manufacturing the same, and more particularly to an intraocular lens capable of providing full-range continuous vision with sufficiently close near-vision and a method for manufacturing the same. The present invention also relates to an artificial lens, and more particularly to an artificial lens that utilizes excessive resolution to achieve focal extension. The artificial lens of the present invention can be embodied as an intraocular lens for implanting into the interior of a human eye and can also be embodied as a contact lens for wearing on the exterior of a human eye, wherein the intraocular lens for implanting into the interior of the human eye includes an aphakic intraocular lens for replacing the natural lens of a cataract patient and a phakic intraocular lens for implanting into a phakic eye to realize a refractive correction function. The present invention also relates to a method for manufacturing an artificial lens.

BACKGROUND

Cataract is a common senile disease, the incidence rate of cataract for people reaching a certain age is almost 100 percent, and the cataract is the number one killer of blindness-causing diseases worldwide. It is the only effective treatment for cataract to take out the opacified natural lens and implant an intraocular lens through surgical operation. With improvement of living standard of people, cataract surgery is gradually changed from a vision recovery surgery to a refractive correction surgery, and patients not only need to be able to see but also need to see clearly, durably and comfortably, so that requirements of different visual functions should be met. Among these requirements, Getting rid of the presbyopic glasses is an important one in many postoperative visual function requirements of cataract patients. After a cataract patient is implanted with a conventional monofocal intraocular lens, the patient looks far and clearly after an operation, but needs to wear a presbyopic glasses when seeing close. Various multifocal intraocular lenses are important development directions for meeting the requirements of the eye after operation for getting rid of the presbyopic glasses. The multifocal intraocular lens is an intraocular lens which distributes optical energy to different focal points by diffraction or regional refraction to realize far vision and near vision and solve the problem of lack of mid-range vision and near vision of a patient. Modern multifocal intraocular lenses have emerged in various forms as modern ophthalmic technology advances. The bifocal intraocular lens is the first to appear, provides two independent focal points for human eyes by diffraction or refraction, is divided into a plurality of additional refractive powers according to different near vision distances of the human eyes. For example, a multifocal intraocular lens with an additional refractive power of +4.0D can realize a near vision distance of about 32 cm for the human eyes and can provide far vision simultaneously, and a multifocal intraocular lens with an additional refractive power of +3.0D can realize a near vision distance of about 42 cm for the human eyes and can provide far vision simultaneously. However, the vision of such multifocal intraocular lenses is discontinuous with the mid-range vision lost, and glare is a common issue and is difficult for patients to accommodate due to the fact that the two focal points are far apart from each other and sharp and have a large influence on each other. Subsequent multifocal intraocular lenses began to try to provide continuous vision in mainly two ways. One is a 'stepless zoom' mode, namely, an intraocular lens of Symfoni ZXR00 model (U.S. Pat. No. 8,747,466B2) of Johnson & Johnson, the additional refractive power of the multifocal intraocular lens is designed to be +1.5D, and two focal points of the lens are connected by means of the 1.5D depth of field of the human eye, so that a full-range vision is realized. However, such intraocular lens is disadvantageous in that the near vision ability is insufficient, having an additional refractive power is only +1.5D, with the unilateral 0.75D depth of field of the human eye, can realize an additional refractive power of +2.25D, corresponding to a near vision distance of about 58 cm from the human eye, so that presbyopic glasses still need to be worn under actual near vision condition, such as reading books and newspapers, and the purpose of removing the glasses is not realized. The other is a trifocal intraocular lens, typically an Acri.lisa trifocal intraocular lens from ZEISS, with a near vision additional refractive power of +3.33D and a mid-range vision additional refractive power of +1.67D, enabling three focal points, far, mid and near, with an adequate near vision distance, with a mid-range vision, but with a discontinuous vision range, and with optical energy distributed to three focal points, less optical energy is acquired at each focal point and the image plane is darker. Foreign companies are also developing intraocular lenses having more focal points, such as four focal points, five focal points. Common characteristics of such multifocal intraocular lenses lie in that the distance between focal points becomes smaller, which allows the depth of field of the human eye to connect the focal points. With more focal points, the energy obtained by each focal point decreases, and the focal points become smoother, so that glare interference of the human eye also decreases accordingly. However, it is a common problem that the image plane becomes darker.

Multifocal intraocular lenses are still in the stage of developing new solutions, and many solutions emerge, but it is still a common goal in the industry to find a continuous, adequate near-vision distance, low-glare and bright-image-plane solution.

When the human eyes have ametropia, various artificial lenses can be adopted for correction. The artificial lens for vision correction mainly includes several types, one of which is not in direct contact with human eyes, typically various types of frame glasses; one is a contact lens that comes into contact with human eye tissue such as the cornea, and various intraocular lenses that are surgically implanted into the interior of the human eye. Another aspect of the present invention is directed generally to an ophthalmic artificial lens in contact with human eye tissue.

An intraocular lens is an intraocular implant, and includes an aphakic intraocular lens used for replacing a natural lens removed from a cataract patient, or a phakic intraocular lens implanted into a phakic eye to realize refractive correction. The aphakic intraocular lens is mainly used for correcting the vision of the aphakic eye after cataract operation and is divided into an anterior chamber type and a posterior chamber type according to implantation position, and the optical zone generally has positive diopter and generally has a biconvex or concave-convex geometry. The phakic intraocular lens is divided into an anterior chamber type and a posterior chamber type according to implantation position. The anterior chamber phakic intraocular lens refers to an intraocular lens implanted in front of the iris of a patient, being fixed by iris clamping or chamber angle supporting.

The posterior chamber phakic intraocular lens refers to an intraocular lens implanted behind the iris and in front of the natural lens, being fixed in the human eye by means of the ciliary sulcus or suspended in the human eye in a floating way. Phakic intraocular lenses are often used for myopia correction in highly myopes, and the optical zone is typically of negative refractive power, typically of either an anterior plano-posterior concave or bi-concave design, and may also be of an astigmatic design, depending on the application.

Intraocular lenses are classified into various types according to the optical function they perform, including: monofocal intraocular lenses aimed at achieving optimal far vision, such as spherical and aspherical intraocular lenses, or Toric monofocal intraocular lenses incorporating astigmatism correction, and the like; various multifocal intraocular lenses aiming at realizing far, mid-range and near vision; and accommodating intraocular lenses aimed at achieving full-range vision, and the like.

Cataract patients generally experience vision problems such as blurred vision, brightness reduction, contrast sensitivity reduction and the like for a long time before operation. The spectrum transmittance of the natural lens of middle-aged and old people is lower than that of young people. Many patients have discomforts such as photophobia, dizziness and the like after implanting a monofocal intraocular lens, because the monofocal intraocular lens projects complete light energy onto the retina, and the image brightness and definition are too high for the patients. Furthermore, monofocal intraocular lenses provide resolution above the limit of human eye resolution, resulting in excessive resolution. Clinically, a yellow intraocular lens for preventing blue light can be used to relieve photophobia to a certain extent, but chromatic aberration problem is raised due to filtering of part of color vision sensitive light, and the excessive resolution provided by the intraocular lens cannot be effectively utilized. In addition, for the patients who have been implanted with monofocal intraocular lenses, they are confronted with a common problem of lack of mid-range vision and near vision. The patients cannot see objects at any distance other than the far focal point, and the life quality of the patients is influenced.

The multifocal intraocular lens is an intraocular lens which distributes optical energy to different image points by diffraction or regional refraction to realize the functions of looking far and looking near and solves the problem of lack of mid-range vision and near vision of a patient. According to different settings of image points, it can be divided into bifocal intraocular lens, trifocal intraocular lens, etc. The problems of dark image surfaces, glare, discontinuous image points and the like generally exist due to light energy distribution mechanism of the multifocal intraocular lens. The image surfaces are mutually interfered and the light energy is lost, so that the resolution is rapidly reduced within the limit of resolution recognizable by human eyes. Various aberrations are clearly perceived by the retina. Both the far vision and the near vision are poor. Such multifocal intraocular lens is considered as a transition product in the process of obtaining full-range vision.

On the basis of that, a large depth of field intraocular lens is derived, which is an intraocular lens having a certain additional refractive power, capable of providing a small amount of near vision distance and performing near vision distance extension by using a part of depth of field of human eyes, and capable of solving the problem of discontinuous image points. The large depth of field intraocular lens is mainly classified into two types, one of which is designed to have a very small additional refractive power by a design method similar to that of a multifocal intraocular lens, typically a Symfony ZXR00 intraocular lens (U.S. Pat. No. 8,747,466B2) by AMO Inc., but the disadvantages in glare are not improved similar to the multifocal intraocular lens and the near vision distance is very limited; the other type adopts intervention of high-order aberrations, but the high-order aberrations are limited by the pupil size, the larger the pupil size, the stronger the near vision effect, with very limited effect under a common pupil size, such as a pupil within 3 mm, while under the condition of large pupil size, the resolution is too poor, causing glare interference.

At present, no intraocular lens can effectively and reasonably utilize excessive resolution to extend the depth of field of human eyes.

Contact lenses are worn on the exterior of the human eye in contact with the eye tissue for correction of refractive conditions of the eye's imaging system. The contact lens is classified into corneal contact lens and scleral contact lens. The corneal contact lens is an ophthalmic contact lens which only covers on the corneal and is not in contact with the sclera. The corneal contact lens is divided into hard corneal contact lens and soft corneal contact lens, wherein the hard corneal contact lens is commonly called "RGP", and the soft corneal contact lens is commonly called "contact lens". The scleral contact lens is a contact lens that covers both the cornea and a portion of the sclera. The contact lens generally has negative diopter, the optical portion has an anterior surface and a posterior surface, and the shape of the posterior surface is consistent with the cornea of human eyes or the cornea and sclera of human eyes and is a concave surface; the anterior surface is used to achieve refractive power and is typically convex. In accordance with the optical performance, the contact lens mainly includes monofocal contact lens, Toric contact lens and multifocal contact lens. The monofocal contact lens is mainly used for correcting hyperopia or myopic ametropia. The Toric contact lens is mainly used for correcting ametropia incorporating astigmatism. The multifocal contact lens is used mainly for vision correction of presbyopia or accommodative deficient eyes, and provide both far vision and near vision zone refractive power, and in some cases, mid-range vision zone refractive power. Although multifocal contact lenses provide vision improvement for many presbyopic subjects, sufficiently effective vision is only obtained when the lens achieves and maintains sufficient dynamic characteristics, i.e., sufficient movement over the surface of the cornea. Even so, in obtaining the above results, a separation of the radiant energy flux occurs, that is, the radiant energy flux is effectively separated by two zones of different refractive powers, thereby causing a loss of visual ability for the wearer with respect to both transitional vision and night vision and producing a secondary or "ghost" image. Providing the wearer with both clear far vision acuity and clear near vision acuity remains a challenge, not to mention reducing or avoiding visual discomfort or visual impairment while achieving this goal.

At present, no contact lens can effectively and reasonably utilize excessive resolution to extend the depth of field of human eyes.

SUMMARY

According to a first aspect of the present invention, there is provided an intraocular lens having an optical portion with an anterior surface and a posterior surface, one of the anterior surface and the posterior surface comprising an aspherical surface and the other of the anterior surface and the posterior surface comprising a multifocal structure that provides the intraocular lens with two or more focal points, such that a through focus response curve of the intraocular lens at a spatial frequency of 50 lp/mm and at a 3 mm aperture has two or more peaks, wherein at least one pair of adjacent peaks of the two or more peaks corresponds to a difference in refractive power which has an absolute value greater than or equal to 1.6D and a minimum value of MTF between the at least one pair of adjacent peaks is greater than or equal to 0.05.

In some embodiments, an expression of a curve of the aspherical surface on a plane rZ of the two-dimensional coordinate system is as follows:

$$z(r) = \frac{\frac{1}{R} * r^2}{1 + \left(1 - (1+Q) * \left(\frac{1}{R}\right)^2 * r^2\right)^{\frac{1}{2}}} + \sum_{i=m}^{n} A_{2i} * r^{2i}$$

wherein R is the radius of curvature of the basal spherical surface of the aspherical surface, r is the perpendicular distance from a point on the curve to the abscissa axis (Z), z is the perpendicular distance from the point on the curve to the ordinate axis (r), $A_{2i}$ is aspherical high-order term coefficient, m and n are both integers not less than 1 and n>m, Q is aspherical coefficient, wherein points on the aspherical surface are obtained in a way that the curve rotates about the abscissa axis (Z) for symmetry variation, wherein the aspherical surface is defined by a scale factor η which is a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface at r=1.5 mm and r=1.0 mm is 1.02 to 1.93, preferably 1.04 to 1.86, and more preferably 1.06 to 1.86.

In some embodiments, the at least one pair of adjacent peaks of the through focus response curve of the intraocular lens at a spatial frequency of 50 lp/mm and at a 3 mm aperture corresponds to a difference in refractive power which has an absolute value of 1.6D to 2.8D, preferably 2.0D to 2.5D, more preferably 2.2D to 2.5D, and more preferably 2.4 to 2.5D.

In some embodiments, the aspherical surface is located centrally within 5 mm, preferably within 4 mm and more preferably within 3 mm in diameter of the optical portion of the intraocular lens.

In some embodiments, the intraocular lens has 2 or 3 focal points.

In some embodiments, the multifocal structure comprises a plurality of diffractive rings, wherein the diffractive ring closest to the centre of the optical portion has a radius of 0.59 to 0.80 mm, preferably 0.63 to 0.72 mm, more preferably 0.63 to 0.68 mm, and more preferably 0.63 to 0.64 mm.

In some embodiments, the number of diffractive rings of the intraocular lens within 3 mm in diameter of the optical portion is 3 to 7, preferably 4 to 5, and more preferably 5.

In some embodiments, the height of the diffractive rings is 1.02 to 2.66 μm.

According to the first aspect of the present invention, there is also provided a method for manufacturing an intraocular lens having an optical portion with an anterior surface and a posterior surface, the intraocular lens having two or more focal points, the method comprising:

(1) determining a depth of field of a human eye;

(2) determining refractive powers respectively corresponding to the two or more focal points of the intraocular lens, such that at least one pair of adjacent focal points of the two or more focal points corresponds to a difference in refractive power which has an absolute value greater than or equal to 1.6D;

(3) determining an aspherical surface such that a depth of field provided by the aspherical surface and the absolute value of the difference in refractive power of the at least one pair of adjacent focal points of the two or more focal points satisfy the following relationship:

the depth of field of the human eye plus the depth of field provided by the aspherical surface is greater than or equal to the absolute value of the difference in refractive power of the at least one pair of adjacent focal points;

(4) manufacturing an intraocular lens such that one of the anterior surface and the posterior surface comprises the aspherical surface determined in step (3) and the other of the anterior surface and the posterior surface comprises a multifocal structure providing two or more focal points each having a respective refractive power determined in step (2).

In some embodiments, in step (3), the aspherical surface is determined such that the depth of field provided by the aspherical surface and the absolute value of the difference in refractive power of the at least one pair of adjacent focal points of the two or more focal points satisfy the following relationship:

the depth of field of the human eye plus the depth of field provided by the aspherical surface is equal to the absolute value of the difference in refractive power of the at least one pair of adjacent focal points.

In some embodiments, step (4) further comprises manufacturing the intraocular lens such that a minimum value of MTF between at least one pair of adjacent peaks of a through focus response curve of the intraocular lens at a spatial frequency of 50 lp/mm and at a 3 mm aperture is greater than or equal to 0.05.

A second aspect of the present invention relates to an artificial lens. The artificial lens of the second aspect of the present invention reasonably makes use of the excessive resolution of the prior art monofocal artificial lens, takes the visual range which can be obtained by the artificial lens eye as a threshold value, and uses an aspherical surface to provide the artificial lens with focal shifting capability, thereby expanding the depth of field of the artificial lens eye. After the human eye is implanted or worn with the artificial lens of the second aspect of the present invention, the human eye can obtain a full range vision from far vision, mid-range vision and near vision without pupil dependence and without glare interference, and comfortable vision quality after the surgery/wearing process, on the premise of not influencing the vision resolution.

According to a first embodiment of the second aspect of the present invention, there is provided an artificial lens having an optical portion comprising a focal extension zone at the center, an anterior surface and/or a posterior surface of the focal extension zone being an aspherical surface, an expression of a curve of the aspherical surface on a plane rZ of the two-dimensional coordinate system is as follows:

$$z(r) = \frac{\frac{1}{R}*r^2}{1+\left(1-(1+Q)*\left(\frac{1}{R}\right)^2*r^2\right)^{\frac{1}{2}}} + \sum_{i=m}^{n} A_{2i}*r^{2i}$$

wherein R is the radius of curvature of the basal spherical surface of the aspherical surface, r is the perpendicular distance from a point on the curve to the abscissa axis (Z), $A_{2i}$ is aspherical high-order term coefficient, m and n are both integers not less than 1 and n>m, Q is aspherical coefficient, wherein points on the aspherical surface are obtained in a way that the curve rotates about the abscissa axis (Z) for symmetry variation, wherein an absolute value of a difference in refractive power |ΔD| of the artificial lens at r=1.5 mm and r=1.0 mm is greater than or equal to 0.50D.

According to the first embodiment of the second aspect of the present invention, in the second embodiment of the second aspect of the present invention, the difference in refractive power ΔD of the artificial lens at r=1.5 mm and r=1.0 mm is greater than or equal to 0.50D.

According to the first embodiment of the second aspect of the present invention, in the third embodiment of the second aspect of the present invention, the artificial lens has an MTF of 0 to 0.42, preferably 0.13 to 0.37, and more preferably 0.13 to 0.28 at a spatial frequency of 100 lp/mm and at a 3 mm aperture in a human eye model.

According to the first embodiment of the second aspect of the present invention, in the fourth embodiment of the second aspect of the present invention, the artificial lens is embodied as an aphakic intraocular lens for replacing a natural lens of a cataract patient.

According to the fourth embodiment of the second aspect of the present invention, in the fifth embodiment of the second aspect of the present invention, an absolute value of the difference in refractive power |ΔD| of the aphakic intraocular lens at r=1.5 mm and r=1.0 mm is 0.60D to 2.70D, preferably 1.00D to 2.70D.

According to the fourth embodiment of the second aspect of the present invention, in the sixth embodiment of the second aspect of the present invention, the difference in refractive power ΔD of the aphakic intraocular lens at r=1.5 mm and r=1.0 mm is 0.60D to 2.49D, preferably 1.00D to 2.49D.

According to the fourth embodiment of the second aspect of the present invention, in the seventh embodiment of the second aspect of the present invention, an asphericity of the aphakic intraocular lens is characterized by a difference in height of the aspherical surface at r=1.5 mm and r=1.0 mm, namely:

ΔZ=Z(r=1.5)−Z(r=1.0)

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the aphakic intraocular lens at r=1.5 mm and r=1.0 mm is 0.002 to 0.138 mm, preferably 0.003 to 0.138 mm, and more preferably 0.004 to 0.138 mm.

According to the fourth embodiment of the second aspect of the present invention, in the eighth embodiment of the second aspect of the present invention, the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\frac{r^2+z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.44 to 10.00, preferably 0.46 to 10.00.

According to the fourth embodiment of the second aspect of the present invention, in the ninth embodiment of the second aspect of the present invention, the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2+z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.44 to 0.99, preferably 0.46 to 0.99.

According to the first embodiment of the second aspect of the present invention, in the tenth embodiment of the second aspect of the present invention, the artificial lens is embodied as a phakic intraocular lens implanted into a phakic eye for refractive correction.

According to the tenth embodiment of the second aspect of the present invention, in the eleventh embodiment of the second aspect of the present invention, an absolute value of the difference in refractive power |ΔD| of the phakic intraocular lens at r=1.5 mm and r=1.0 mm is 0.50D to 4.04D, preferably 0.84D to 4.04D.

According to the tenth embodiment of the second aspect of the present invention, in the twelfth embodiment of the second aspect of the present invention, the difference in refractive power ΔD of the phakic intraocular lens at r=1.5 mm and r=1.0 mm is 0.50D to 3.06D, preferably 1.01D to 3.06D.

According to the tenth embodiment of the second aspect of the present invention, in the thirteenth embodiment of the second aspect of the present invention, an asphericity of the phakic intraocular lens is characterized by a difference in height of the aspherical surface at r=1.5 mm and r=1.0 mm, namely:

$$\Delta Z = Z(r=1.5) - Z(r=1.0)$$

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the phakic intraocular lens at r=1.5 mm and r=1.0 mm is 0.009-0.146 mm.

According to the tenth embodiment of the second aspect of the present invention, in the fourteenth embodiment of the second aspect of the present invention, the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.74 to 1.23, preferably 1.01 to 1.23.

According to the first embodiment of the second aspect of the present invention, in the fifteenth embodiment of the second aspect of the present invention, the artificial lens is embodied as a contact lens worn outside the human eye.

According to the fifteenth embodiment of the second aspect of the present invention, in the sixteenth embodiment of the second aspect of the present invention, an absolute value of the difference in refractive power |ΔD| of the contact lens at r=1.5 mm and r=1.0 mm is 0.50D to 1.515D, preferably 0.627D to 1.515D.

According to the fifteenth embodiment of the second aspect of the present invention, in the seventeenth embodiment of the second aspect of the present invention, the difference in refractive power ΔD of the contact lens at r=1.5 mm and r=1.0 mm is 0.50D to 1.445D, preferably 0.627D to 1.445D.

According to the fifteenth embodiment of the second aspect of the present invention, in the eighteenth embodiment of the second aspect of the present invention, an asphericity of the contact lens is characterized by a difference in height of the aspherical surface at r=1.5 mm and r=1.0 mm, namely:

$$\Delta Z = Z(r=1.5) - Z(r=1.0)$$

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the contact lens at r=1.5 mm and r=1.0 mm is 0.0389 to 0.0946 mm, preferably 0.0431 to 0.0946 mm.

According to the fifteenth embodiment of the second aspect of the present invention, in the nineteenth embodiment of the second aspect of the present invention, the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.978 to 1.026, preferably 0.978 to 0.99.

According to any of the first embodiment to the nineteenth embodiment of the second aspect of the present invention, in the twentieth embodiment of the second aspect of the present invention, wherein the focal extension zone is spanned within a diameter of less than or equal to 4.0 mm, preferably within a diameter of less than or equal to 3.5 mm, and more preferably within a diameter of less than 3.0 mm.

According to any of the first embodiment to the nineteenth embodiment of the second aspect of the present invention, in the twenty-first embodiment of the second aspect of the present invention, the optical portion of the artificial lens further comprises an annular transition zone outside the focal extension zone and an annular aberration correction zone outside the transition zone, wherein the aberration correction zone serves for aberration modification and correction and the transition zone provides a smooth transition in refractive power of the artificial lens.

According to the twenty-first embodiment of the second aspect of the present invention, in the twenty-second embodiment of the second aspect of the present invention, the transition zone has a width greater than or equal to 0.25 mm, preferably 0.25 to 2.0 mm, and more preferably 0.25 to 1.0 mm.

According to the twenty-first embodiment of the second aspect of the present invention, in the twenty-third embodiment of the second aspect of the present invention, the transition zone is a combination of a plurality of annular regions.

According to a twenty-fourth embodiment of the second aspect of the present invention, there is also provided a method for manufacturing an artificial lens capable of achieving focal extension by making use of excessive resolution of the human eye, the method comprising the steps of:

(1) determining a resolution limit d of an artificial lens eye according to a vision requirement of the artificial lens eye;

(2) determining a spatial cut-off frequency $f_j$ of the artificial lens eye according to the resolution limit d of the artificial lens eye;

(3) determining an MTF value MTF($f_i$) of a desired spatial frequency $f_i$ according to the spatial cut-off frequency $f_j$ and a curve MTF(1) between the MTF and the spatial frequency f, wherein the curve MTF(1) between the MTF and the spatial frequency f is expressed as MTF (f)=$a_0$+$a_1$f+$a_2f^2$+ . . . $a_nf^n$, where $a_0$, $a_1$, $a_2$, . . . $a_n$ are polynomial coefficients; and (4) manufacturing an artificial lens such that a minimum MTF value of the artificial lens at the desired spatial frequency $f_i$ and at a 3 mm aperture in a human eye model is the MTF(f).

According to the twenty-fourth embodiment of the second aspect of the present invention, in the twenty-fifth embodiment of the second aspect of the present invention, step (4) further comprises manufacturing the artificial lens such that an artificial lens eye having the artificial lens achieves a vision that: using "rolling E" optotype and decimal vision for recording, the vision VA is 0.5 to 1.2, preferably 0.5 to 1.0, and more preferably 0.5 to 0.8.

According to the twenty-fourth embodiment of the second aspect of the present invention, in the twenty-sixth embodiment of the second aspect of the present invention, step (4) further comprises manufacturing the artificial lens such that the artificial lens has an MTF of 0 to 0.42, preferably 0.13 to 0.37, and more preferably 0.13 to 0.28 at a spatial frequency of 100 lp/mm and at a 3 mm aperture in a human eye model.

Terminology

Refractive power of an intraocular lens refers to the reciprocal of the focal length of paraxial light having a wavelength of 546.07 nm in the intraocular condition, in units of the reciprocal of meters ($m^{-1}$), which is expressed in "diopters" by the symbol "D".

Far refractive power of an intraocular lens refers to the refractive power by which a distant object is imaged.

Near refractive power of an intraocular lens refers to the refractive power by which a near object is imaged.

Additional refractive power of an intraocular lens refers to the difference between the refractive power of the intraocular lens by which an object other than the far focal point is imaged and the far refractive power.

Bifocal intraocular lens has a far refractive power and a near refractive power, and the difference of the far refractive power and the near refractive power is the additional refractive power; trifocal intraocular lens has a far refractive power, a middle refractive power, and a near refractive power, wherein the difference between the middle refractive power and the far refractive power is the mid-range additional refractive power, and the difference between the near refractive power and the far refractive power is the near additional refractive power; and so on.

More generally, the difference of refractive power between different focal points is expressed in the difference between diopters.

Through focus response curve refers to a curve drawn as follows: the intraocular lens is placed in an ISO standard human eye model, under a certain measuring aperture and a certain spatial frequency, MTFs of the intraocular lens at different positions of an imaging optical path are measured, the obtained MTFs are used as ordinates, and the positions on the imaging optical path are used as abscissas, so as to draw the curve. In some cases, the positions on the imaging optical path are expressed in diopters, i.e., the abscissas are diopters in units of D. The positions on the imaging optical path are converted into diopters by the following formula:

$$\frac{L_0}{D_0} = \frac{L_0 + \Delta L}{D_0 + \Delta D}$$

wherein, $L_0$ represents the position of a certain focal point on the optical path in units of meters or millimeters, $D_0$ represents the refractive power of a certain focal point of the intraocular lens in units of D; $\Delta L$ represents the distance between a certain point on the optical path and a certain focal point of the intraocular lens, $\Delta D$ represents the difference of refractive powers between the respective point and the certain focal point;

wherein $\Delta D$ is the defocal amount, which refers to a distance between different positions on the imaging optical path and a certain focal point in the through focus response curve, and when converted into diopter, refers to a diopter difference between the different positions on the imaging optical path and the certain focal point. In some cases, in order to reflect the defocal amount more clearly, the diopter of the certain focal point is set as the origin of abscissa.

Focal point continuity means that the MTF minimum between two adjacent peaks of the through focus response curve (which correspond to two adjacent focal points) is greater than or equal to 0.05 at a spatial frequency of 50 lp/mm.

Aphakic intraocular lens: an intraocular artificial lens for replacing the removed natural lens of a cataract patient to correct the refractive condition of an aphakic eye after cataract surgery.

Phakic intraocular lens: an intraocular artificial lens for correcting ametropia of a phakic eye.

Contact lens: an artificial lens worn on a corneal or scleral surface for correcting ametropia of a human eye.

Artificial lens eye: the eye after implanting with an artificial lens or wearing an artificial lens outside of the eye, without any other vision correction measures.

Furthermore, unless defined otherwise, all technical and scientific terms used herein have the same meaning as commonly understood by one of ordinary skill in the art to which this invention belongs. In the event of inconsistencies, this specification and the definitions included herein will prevail.

BRIEF DESCRIPTION OF THE DRAWINGS

FIGS. 19a and 19b show a comparison of American military standard full optotype measurements of an intraocular lens according to the first aspect of the present invention with Symfony ZXR00 intraocular lens and a prior art trifocal intraocular lens, wherein FIGS. 19a, 19b show the American military standard graphs for −0.9D to 1.2D, 1.5D to 3.6D defocal ranges, respectively.

DETAILED DESCRIPTION OF EMBODIMENTS

Figure 1:
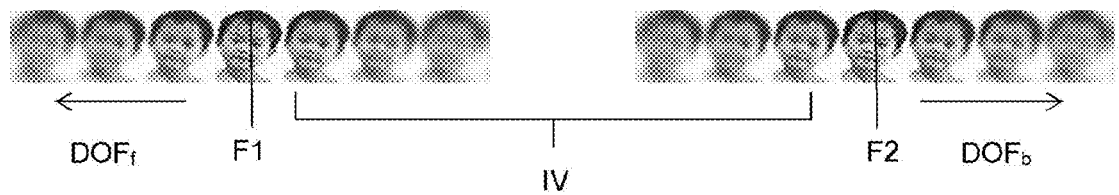
FIG. 1 schematically illustrates mid-range vision provided by a depth of field in the human eye.

The depth of field of human eyes is a phenomenon that human eyes can form a clear image in a certain range in front of and behind a focal point after focusing is finished. Relevant studies have shown that the human eye itself can form a depth of field of approximately 1.5D around the focal point. As shown in FIG. 1, where F1 is the near focal point of human eye, F2 is the far focal point of human eye, the distance between the far focal point and the near focal point is referred to as middle viewing range, and the vision of human eye in middle viewing range is referred to as mid-range vision (IV). The depth of field of the human eye acts on the far focal point and the near focal point, respectively, and simultaneously provides unilateral depth of field on two sides of the far focal point and the near focal point, respectively. The unilateral depth of field, in which vision in a direction closer than the focal point is provided, is called a front depth of field ($DOF_f$), and the unilateral depth of field, in which vision in a direction farther than the focal point is provided, is called a back depth of field ($DOF_b$). For multifocal intraocular lenses, the back depth of field of the near focal point and the front depth of field of the far focal point provide a certain mid-range vision.

If the depth of field of the human eye functions alone, a depth of field of 0.75D can be provided at the far focal point in a direction toward the near focal point and at the near focal point in a direction toward the far focal point, respectively. The depth of field enables focal point continuity when the additional refractive power of the multifocal intraocular lens is set to ≤1.5D. This design principle is adopted by the Symfony ZXR 00 of Johnson & Johnson. However, the depth of field of the human eye is so limited that the near focal point design limit of the multifocal intraocular lens is severely restrained, rending the near vision insufficient.

Figure 2A:
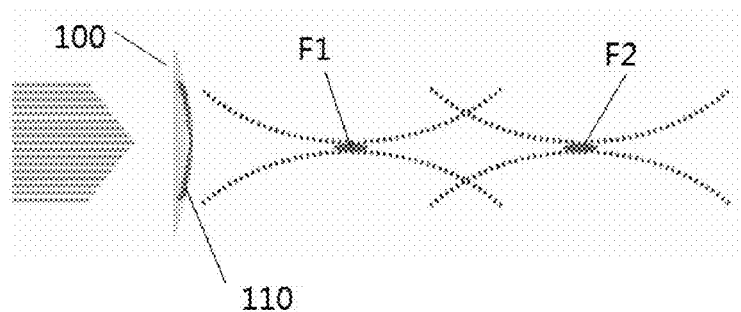
FIGS. 2a to 2c schematically illustrate the inventive idea of the first aspect of the present invention, wherein FIG. 2a schematically illustrates that the multifocal structure of the intraocular lens provides two focal points, FIG. 2b schematically illustrates that the aspherical surface of the intraocular lens provides an extension of the depth of field, and FIG. 2c schematically illustrates that a continuous viewing range between two adjacent focal points is achieved under the combined action of the multifocal structure and the aspherical surface.
Figure 2B:
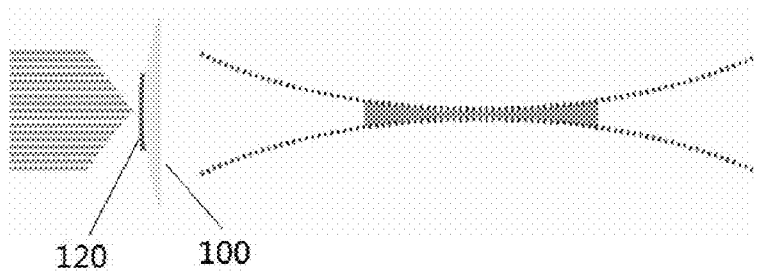
Figure 2C:
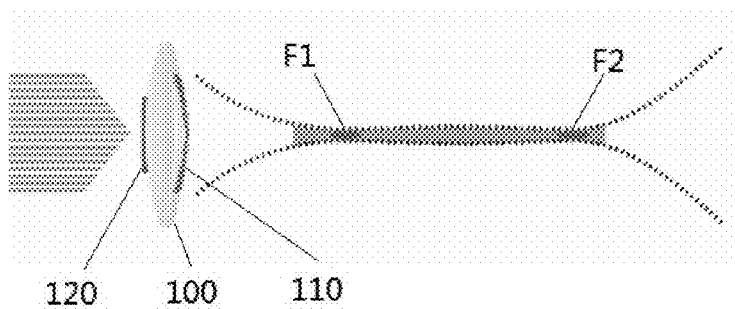

The first aspect of the present invention is discussed in detail below. In the first aspect, the present invention provides an intraocular lens having anterior and posterior optical surfaces. One of the optical surfaces has a multifocal structure providing two or more focal points, and the other optical surface has an aspherical surface. Within a conventional diameter used in the intraocular lens, such as a typical diameter of 3 mm, the aspherical surface uniformly distributes light rays on a certain range which would otherwise be concentrated on one point, so as to form unilateral depth of field extension at each focal point in a closer direction. On one hand, the depth of field extension, in combination with the depth of field of human eyes, connects at least one pair of adjacent focal points of two or more focal points to realize continuous vision between the at least one pair of adjacent focal points. On the other hand, the depth of field extension expands the near focal point to be closer to realize sufficient near vision capability. FIGS. 2a to 2c schematically illustrate the inventive idea of the first aspect of the present invention, wherein FIG. 2a schematically illustrates that the multifocal structure 110 of the intraocular lens 100 provides a near focal point F1 and a far focal point F2, FIG. 2b schematically illustrates that the aspherical surface 120 of the intraocular lens 100 provides an extension of the depth of field, and FIG. 2c schematically illustrates that a continuous viewing range between two adjacent focal points F1 and F2 is achieved under the combined action of the multifocal structure 110 and the aspherical surface 120. In FIG. 2a and FIG. 2c, the multifocal structure 110 includes a plurality of diffractive rings. The multifocal structure of the intraocular lens of the first aspect of the present invention may also be achieved by refraction, such as annular regional refraction, sector regional refraction, and the like.

Figure 4A:
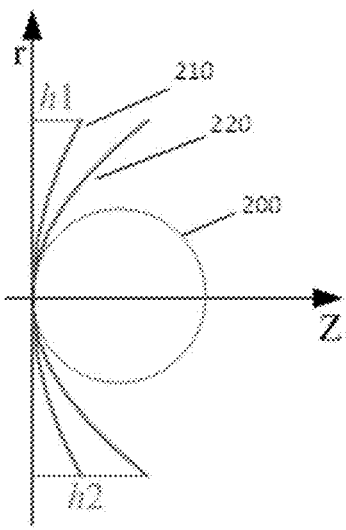
FIG. 4a shows the difference in the curves of an aspherical surface used in the first aspect of the present invention, a prior art aspherical surface and a spherical surface.
Figure 4B:
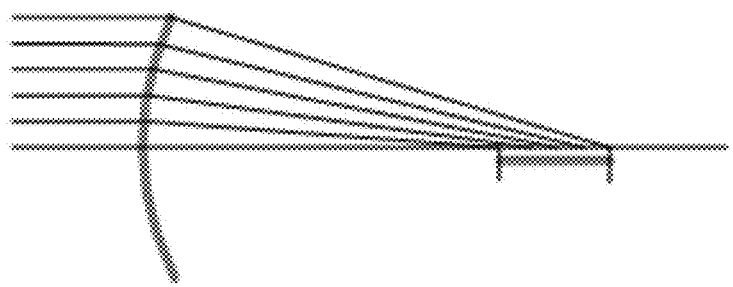
FIG. 4b shows a schematic drawing of elongating of the focal point by an aspherical surface used in the first aspect of the present invention.

One optical surface of the intraocular lens according to the first aspect of the present invention comprises an aspherical surface which precisely distributes the light rays by changes in surface shape, elongating the focal point. FIG. 4a shows the differences in the curves of the aspherical surface 210 used in the first aspect of the present invention, the prior art aspherical surface 220 and the spherical surface 200, and FIG. 4b shows a schematic drawing of elongating of the focal point by an aspherical surface used in the first aspect of the present invention. The expression of the curve of the aspherical surface on the plane rZ of the two-dimensional coordinate system is as follows:

$$z(r) = \frac{\frac{1}{R}*r^2}{1+\left(1-(1+Q)*\left(\frac{1}{2}\right)^2*r^2\right)^{\frac{1}{2}}} + \sum_{i=m}^{n} A_{2i}*r^{2i}$$

wherein R is the radius of curvature of the basal spherical surface of the aspherical surface, r is the perpendicular distance from a point on the curve to the abscissa axis (Z), $A_{2i}$ is aspherical high-order term coefficient, m and n are both integers not less than 1 and n>m, Q is aspherical coefficient, wherein points on the aspherical surface are obtained in a way that the curve rotates about the abscissa axis (Z) for symmetry variation.

The other optical surface of the intraocular lens has a multifocal structure by means of which optical energy incident on the intraocular lens is distributed to two or more focal points. The additional refractive power is used as a measure. There is a conversion relation between the additional refractive power and the near vision distance of the human eyes, and Table 1.1 shows a correspondence relation between the additional refractive power of the multifocal intraocular lens calculated under a standard human eye model and the theoretical near vision distance. Of course, the correspondence relationship has a small range of deviation depending on the condition of the human eye.

TABLE 1.1

| Additional refractive power vs. near vision distance | |
|---|---|
| Additional refractive power | Theoretical near vision distance/cm |
| +2.0 D | 64 |
| +2.4 D | 54 |
| +2.8 D | 46 |
| +3.2 D | 40 |
| +3.6 D | 35 |
| +4.0 D | 32 |

In the technical solution of the first aspect of the present invention, the depth of field provided by the aspherical surface and the diopter difference between adjacent focal points provided by the multifocal structure mutually affect each other. For example, for a multifocal intraocular lens with a far focal point and a near focal point, if the absolute value of the difference of the diopters between the two adjacent focal points of the intraocular lens is too high, the difficulty of aspherical design increases greatly, and the asphericity needs to be increased greatly to realize connection of the focal points, and the large asphericity easily brings aberration interference to the intraocular lens, which affects the imaging quality, and in this case, the additional refractive power provided by the multifocal structure already realizes adequate near vision distance for the human eye, and the extending effect of the aspherical surface on the near focal point is wasted; conversely, if the difference of the diopters between the two focal points is too low, the asphericity may decrease, but the near vision ability is significantly insufficient. Therefore, in order to make the vision range of the multifocal intraocular lens continuous and realize adequate near vision distance, the depth of field provided by the aspherical surface and the difference of the diopter between the adjacent focal points provided by the multifocal structure follow the following relationship:

the depth of field provided by the human eye+the depth of field provided by the aspherical surface≥the absolute value of the difference in refractive power of at least one pair of adjacent focal points.

More preferably, the depth of field provided by the aspherical surface and the difference of the diopter between the adjacent focal points provided by the multifocal structure follow the following relationship:

the depth of field provided by the human eye+the depth of field provided by the aspherical surface=the absolute value of the difference in refractive power of at least one pair of adjacent focal points.

The depth of field of the human eye can be obtained through various ways, including medical measurement statistical data, laboratory human eye model measurement data, or measurement data of each individual. Under general conditions, the depth of field of the human eye in medical statistics is 0.5-1.8D, and under a laboratory ISO standard human eye model, a standard depth of field of the human eye is 1.5D.

Table 1.2 shows the depth of field of the aspherical surface capable of achieving focal point continuity and the additional refractive power matched therewith according to the above relationship. The design value of the total near vision ability obtained by the human eye under the matching relation is the sum of the unilateral depth of field of the human eye (half of the depth of field of the human eye), the depth of field provided by the aspherical surface and the additional refractive power of the intraocular lens. The "clear vision" given in the table refers to the point at which the intraocular lens actually achieves clear vision. In general, multifocal intraocular lenses distribute more optical energy in the far focal point and less in the near focal point, so clear near vision generally occurs at a distance corresponding to the sum of the additional refractive power and the depth of field provided by the aspherical surface, and vision clarity decreases as a result of the optical energy as the distance decreases. In an embodiment of the first aspect of the present invention, clear vision means an MTF of about 0.1 at 50 lp/mm. An MTF of 0.1 at 50 lp/mm can achieve VA vision of about 0.4 for the human eye. When the MTF of human eye at 50 lp/mm is less than 0.05, the MTF can be regarded as being close to 0, and the resolution of human eye is not enough, and the discontinuous point of vision is presented.

TABLE 1.2

Depth of field provided by aspherical surface and additional refractive power matched therewith

| Human eye unilateral depth of field/D | Depth of field provided by aspherical surface/D | Additional refractive power/D | Total near vision/D | Clear vision/D |
|---|---|---|---|---|
| 0.75 | 0.1 | 1.6 | 2.45 | 1.7 |
| 0.75 | 0.2 | 1.7 | 2.65 | 1.9 |
| 0.75 | 0.3 | 1.8 | 2.85 | 2.1 |
| 0.75 | 0.4 | 1.9 | 3.05 | 2.3 |
| 0.75 | 0.5 | 2.0 | 3.25 | 2.5 |
| 0.75 | 0.6 | 2.1 | 3.45 | 2.7 |
| 0.75 | 0.7 | 2.2 | 3.65 | 2.9 |
| 0.75 | 0.8 | 2.3 | 3.85 | 3.1 |
| 0.75 | 0.9 | 2.4 | 4.05 | 3.3 |
| 0.75 | 1.0 | 2.5 | 4.25 | 3.5 |
| 0.75 | 1.1 | 2.6 | 4.45 | 3.7 |
| 0.75 | 1.2 | 2.7 | 4.65 | 3.9 |
| 0.75 | 1.3 | 2.8 | 4.85 | 4.1 |

For multifocal intraocular lenses, a spatial frequency of 50 lp/mm reflects design features well. In the case of a trifocal intraocular lens, a 50 lp/mm through focus response curve would clearly show three peaks. Likewise, a 50 lp/mm through focus response curve for a tetra-focal intraocular lens would show four peaks. In the case of a bifocal intraocular lens, a 50 lp/mm through focus response curve would show two peaks. When the distance between adjacent peaks of the 50 lp/mm through focus response curve of the multifocal intraocular lens is larger than 1.5D, since the focal points are discontinuous, the depth of field of human eyes is not enough to connect the focal points, so that a vision discontinuous point with MTF smaller than 0.05 obviously presents between adjacent peaks.

The intraocular lens of the first aspect of the present invention is significantly distinguished from multifocal intraocular lenses of the prior art in that the intraocular lens of the first aspect of the present invention, due to the presence of the multifocal structure, has a multi-peak structure in a through focus response curve of the intraocular lens at a spatial frequency of 50 lp/mm, at least one pair of adjacent peaks being sufficiently spaced apart, with the spacing for example greater than 1.6D, being 1.6D to 2.8D, preferably 2.0D to 2.5D, more preferably 2.2D to 2.5D, and more preferably 2.4 to 2.5D, and the multifocal structure of the intraocular lens of the first aspect of the present invention cooperates with the large depth of field provided by aspherical surface such that the minimum value of the MTF between at least one pair of adjacent peaks of the through focus response curve is greater than or equal to 0.05 at a spatial frequency of 50 lp/mm, such that there are no visual discontinuities, as shown in FIGS. 7 to 17.

The aspherical surface of the intraocular lens according to the first aspect of the present invention is located within 5 mm, preferably within 4 mm, and more preferably within 3 mm in diameter from the center of the optical portion. The aspherical surface may be located on either of the anterior or posterior surfaces of the optical portion of the intraocular lens. Unlike a normal aspherical surface, the surface shape of the aspherical surface of the intraocular lens according to the first aspect of the present invention differs significantly from that of a spherical surface. This difference in surface shape is defined by a ratio between the height of the surface shape of the aspherical surface at a certain radius of the optical portion and the height of the surface shape of a spherical surface having the same radius of curvature:

$$\rho = \frac{(h - h_0)}{h_0}$$

wherein h represents the height of the surface shape of the aspherical surface at the radius of 1.5 mm of the optical portion, ho represents the height of the surface shape of the spherical surface with the same radius of curvature. The difference between the aspherical surface of the intraocular lens according to the first aspect of the present invention and the spherical surface is significantly larger (by one or more order of magnitudes) than the difference between the conventional aspherical surface and the spherical surface.

TABLE 1.3

Difference between a large depth of field aspherical surface according to the first aspect of the present invention and a conventional aspherical surface

| Refractive index | Type of aspherical surface | Refractive power | Ra | Rp | CT | A4 | A6 | A8 | A10 | ρ | Location of aspherical surface |
|---|---|---|---|---|---|---|---|---|---|---|---|
| 1.48 | large depth of field | 18.0D | 20.50 | −11.10 | 0.73 | −6.729E−04 | −1.540E−05 | 2.733E−06 | −1.976E−08 | 0.14 | Anterior surface |
| 1.48 | conventional | 18.0D | 20.50 | −11.10 | 0.73 | −1.233E−03 | −1.082E−04 | −1.876E−06 | 1.448E−06 | 0.06 | Anterior surface |

Tables 1.4 through 1.22 show some embodiments of the first aspect of the present invention, wherein "basal surface shape" refers to information about intraocular lens refractive index, refractive power, center thickness, anterior and posterior surface radii of curvature, aspherical coefficients, and the diffraction ring parameters refer to the radius and height of the diffraction ring on the intraocular lens.

In some embodiments of the first aspect of the present invention, the aspherical surface provides a depth of field in the range of 0.1D to 1.3D, preferably in the range of 0.5D to 1.0D, and more preferably in the range of 0.7D to 1.0D.

Figure 3:
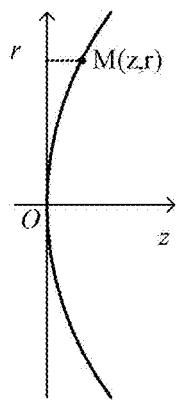
FIG. 3 schematically shows a curve of the aspherical surface on the plane rZ of the two-dimensional coordinate system and a point M thereon.

In some embodiments of the first aspect of the present invention, the aspherical surface is defined by a scale factor η of the equivalent radius of curvature, the scale factor η being the ratio of the equivalent radius of curvature $\overline{R}$ of the aspherical surface at different positions m, n of the curve on the plane rZ of the two-dimensional coordinate system:

$$\eta = \frac{\overline{R}_m}{\overline{R}_n}$$

wherein the equivalent radius of curvature $\overline{R}$ is expressed as:

$$\overline{R} = \frac{r^2 + z^2}{2 \cdot z}$$

where r is the perpendicular distance from a point on the curve to the abscissa axis Z, i.e., the height difference between the point and the vertex of the aspherical surface, and z is the perpendicular distance from the point on the curve to the ordinate axis r, see FIG. 3.

In the first aspect of the present invention, the aspherical surface is defined by a scale factor η, the scale factor η being the ratio of the equivalent radius of curvature $\overline{R}$ of the aspherical surface at different positions m, n of the curve on the plane rZ of the two-dimensional coordinate system. In some embodiments, the asphericity of the intraocular lens is characterized by the scale factor η of the equivalent radius of curvature of the aspherical surface at r=1.5 mm, $\overline{R}_{1.5}$ and the equivalent radius of curvature at r=1.0 mm, $\overline{R}_{1.0}$, namely:

$$\eta = \frac{\overline{R}_{1.5}}{\overline{R}_{1.5}}$$

In some embodiments, the aspherical surface of the intraocular lens of the first aspect of the present invention has a scale factor η between 1.02 and 1.93, preferably between 1.04 and 1.86, more preferably between 1.06 and 1.86, at r=1.5 mm and r=1.0 mm.

The multifocal structure of the intraocular lens of the first aspect of the present invention may be located on either of the anterior or posterior surfaces of the optical portion of the intraocular lens, but not on the same surface as the aspherical surface.

Figure 5:
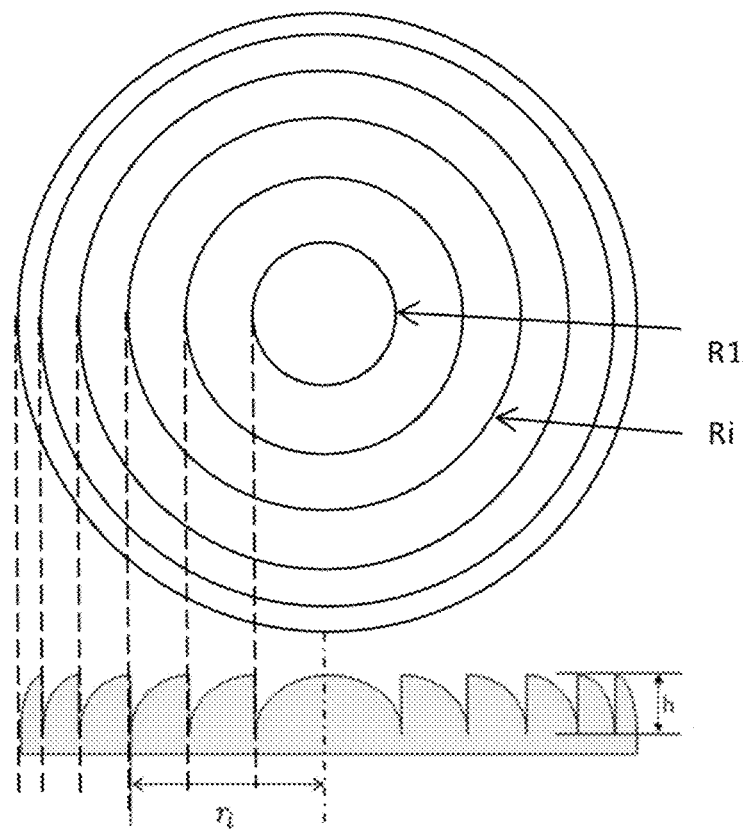
FIG. 5 schematically illustrates the diffractive ring structure and parameters employed by the intraocular lens of the first aspect of the present invention.

In some embodiments, the multifocal structure of the intraocular lens of the first aspect of the present invention comprises a plurality of diffractive rings. In some embodiments, a first diffraction ring of the plurality of diffraction rings has a radius of 0.59 to 0.80 mm, preferably 0.63 to 0.72 mm, more preferably 0.63 to 0.68 mm, and more preferably 0.63 to 0.64 mm. The number of diffractive rings in the range of 3 mm diameter of the optical portion of the intraocular lens of the first aspect of the present invention is 3 to 7, preferably 4 to 5, and more preferably 5. The height of the diffraction rings of the intraocular lens according to the first aspect of the present invention is 1.02 to 2.66 µm. In the first aspect of the present invention, the radius of the diffractive ring refers to the distance between the center of the optical portion and the diffractive ring, and the first diffractive ring refers to the diffractive ring closest to the center of the optical portion. FIG. 5 schematically shows the diffraction ring structure and parameters thereof adopted by the intraocular lens according to the first aspect of the present invention, wherein R1, Ri represent the first and the ith diffraction rings, respectively, ri represents the radius of the ith diffraction ring, and h represents the height of the diffraction ring.

In other embodiments, the multifocal structure of the intraocular lens of the first aspect of the present invention may also be implemented by refraction, such as by annular regional refraction, sector regional refraction, or the like.

Example 1

Figure 7:
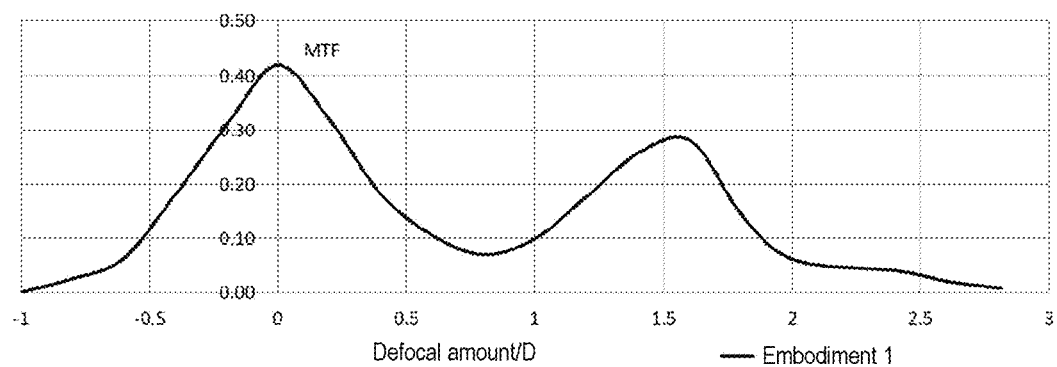
FIG. 7 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.4 and Table 1.5, wherein the basal surface shape comprises the radii of curvature of the anterior and posterior surfaces of the intraocular lens, the central thickness and the aspherical surface coefficients. The refractive index of the material is 1.46, the diffraction bifocal design is adopted, the posterior surface is aspherical, the anterior surface comprises diffraction rings, the radius of the first diffraction ring is 0.80 mm, the height of the diffraction ring is 1.77 µm, the refractive power is 36.0D, the additional refractive power is +1.6D, the depth of field is 0.10D. Clear vision of the near vision distance corresponding to the add power above +1.70D can be realized. The through focus response curve at the frequency of 50 lp/mm and at 3 mm aperture is shown in FIG. 7. The MTF respectively has a peak at the far and near focal points, the minimum MTF between the peaks of the far and near focal points is above 0.05, and the continuous focal point is realized.

TABLE 1.4

Parameters of basal surface shape of example 1

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.46 | 36.0 | 10.00 | −5.21 | 2.00 | 0 | 7.964E−004 | 1.389E−004 | 6.499E−06 | −8.915E−07 | 0.10 | 1.02 | 1.6 | Posterior surface |

TABLE 1.5

Parameters of diffraction rings of example 1

| No. of diffraction ring | Radius of diffraction ring/mm | Height of diffraction ring/μm |
|---|---|---|
| 1 | 0.797545 | 1.77 |
| 2 | 1.130742 | 1.77 |
| 3 | 1.388415 | 1.77 |
| 4 | 1.607372 | 1.77 |
| 5 | 1.801845 | 1.77 |
| 6 | 1.979123 | 1.77 |

Example 2

Figure 8:
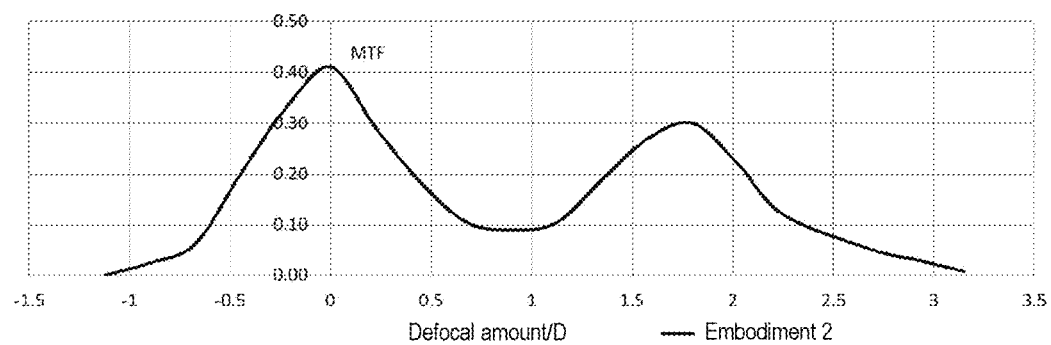
FIG. 8 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.6 and Table 1.7, wherein the refractive index of the material is 1.55, the diffraction bifocal design is adopted, the posterior surface is aspherical, the anterior surface comprises diffraction rings, the radius of the first diffraction ring is 0.75 mm, the height of the diffraction ring is 1.02 μm, the refractive power is 36.0D, the additional refractive power is +1.8D, the depth of field is 0.40D. Clear vision of the near vision distance corresponding to the add power above +2.20D can be realized. The through focus response curve at the frequency of 50 lp/mm and at 3 mm aperture is shown in FIG. 8. The MTF respectively has a peak at the far and near focal points, the minimum MTF between the peaks of the far and near focal points is above 0.05, and is close to 0.10.

TABLE 1.6

Parameters of basal surface shape of example 2

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.55 | 36.0 | 11.55 | −11.82 | 0.90 | −3.59 | −2.871E−04 | 2.745E−06 | 0 | 0 | 0.4 | 1.02 | 1.8 | Posterior surface |

TABLE 1.7

Parameters of diffraction rings of example 2

| No. of diffraction ring | Radius of diffraction ring/mm | Height of diffraction ring/μm |
|---|---|---|
| 1 | 0.754702 | 1.02 |
| 2 | 1.071356 | 1.02 |
| 3 | 1.317229 | 1.02 |
| 4 | 1.52705 | 1.02 |
| 5 | 1.714249 | 1.02 |
| 6 | 1.885712 | 1.02 |
| 7 | 2.045539 | 1.02 |

Example 3

Figure 9:
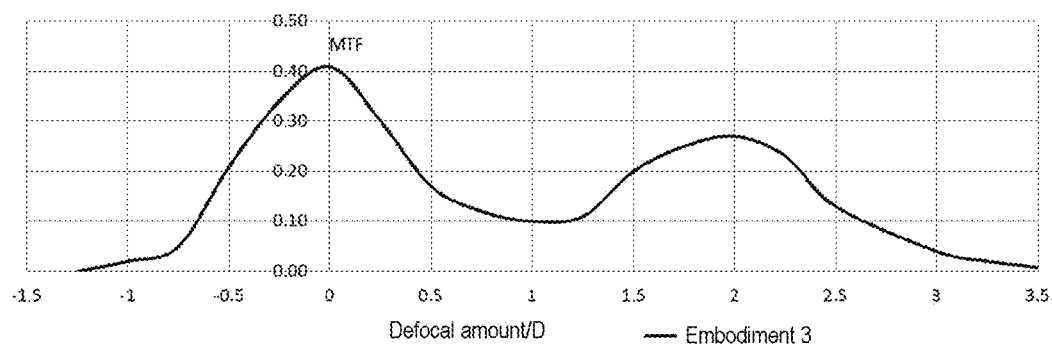
FIG. 9 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.8 and Table 1.9, wherein the refractive index of the material is 1.48, the diffraction bifocal design is adopted, the anterior surface is aspherical, the posterior surface comprises diffraction rings, the radius of the first diffraction ring is 0.71 mm, the height of the diffraction ring is 1.53 μm, the refractive power is 20.0D, the additional refractive power is +2.0D, the depth of field is 0.50D. Clear vision of the near vision distance corresponding to the add power above +2.50D can be realized. The through focus response curve at the frequency of 50 lp/mm and at 3 mm aperture is shown in FIG. 9. The MTF respectively has a peak at the far and near focal points, the minimum MTF between the peaks of the far and near focal points is 0.10.

TABLE 1.8

Parameters of basal surface shape of example 3

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.48 | 20.0 | 17.32 | −11.10 | 0.73 | 0 | −8.757E−04 | −3.602E−05 | 5.011E−06 | −2.886E−08 | 0.5 | 1.04 | 2.0 | Anterior surface |

TABLE 1.9

Parameters of diffraction rings of example 3

| No. of diffraction ring | Radius of diffraction ring/mm | Height of diffraction ring/μm |
|---|---|---|
| 1 | 0.710401 | 1.53 |
| 2 | 1.009176 | 1.53 |
| 3 | 1.241696 | 1.53 |
| 4 | 1.440607 | 1.53 |
| 5 | 1.618539 | 1.53 |
| 6 | 1.78198 | 1.53 |
| 7 | 1.934803 | 1.53 |
| 8 | 2.079551 | 1.53 |

Example 4

Figure 10:
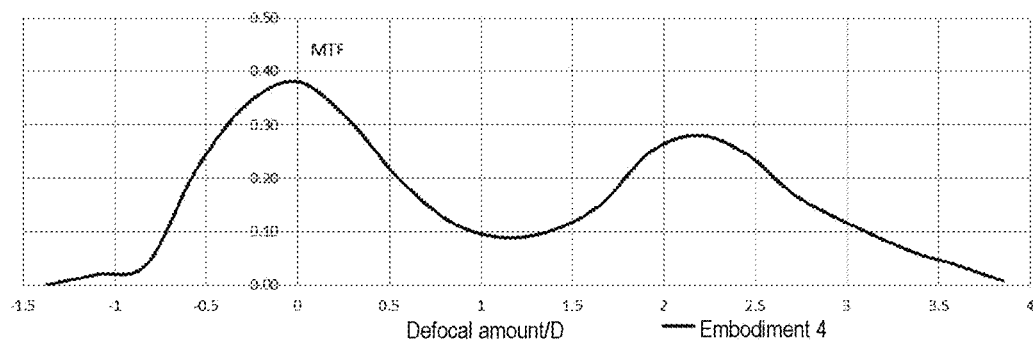
FIG. 10 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.10 and Table 1.11, wherein the refractive index of the material is 1.48, the diffraction bifocal design is adopted, the anterior surface is aspherical, the posterior surface comprises diffraction rings, the radius of the first diffraction ring is 0.68 mm, the height of the diffraction ring is 1.72 μm, the refractive power is 14.0D, the additional refractive power is +2.2D, the depth of field is 0.70D. Clear vision of the near vision distance corresponding to the add power above +2.90D can be realized. The through focus response curve at the frequency of 50 lp/mm and at 3 mm aperture is shown in FIG. 10. The MTF respectively has a peak at the far and near focal points, the minimum MTF between the peaks of the far and near focal points is above 0.05, and is close to 0.10.

TABLE 1.10

Parameters of basal surface shape of example 4

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.48 | 14.0 | 120.00 | −10.00 | 0.90 | 0 | −1.166E−03 | 1.677E−05 | 0 | 0 | 0.7 | 1.86 | 2.2 | Anterior surface |

TABLE 1.11

Parameters of diffraction rings of example 4

| No. of diffraction ring | Radius of diffraction ring/mm | Height of diffraction ring/μm |
|---|---|---|
| 1 | 0.679583 | 1.72 |
| 2 | 0.964908 | 1.72 |
| 3 | 1.186599 | 1.72 |
| 4 | 1.375916 | 1.72 |
| 5 | 1.544951 | 1.72 |
| 6 | 1.699909 | 1.72 |
| 7 | 1.844485 | 1.72 |
| 8 | 1.981104 | 1.72 |

Example 5

Figure 11:
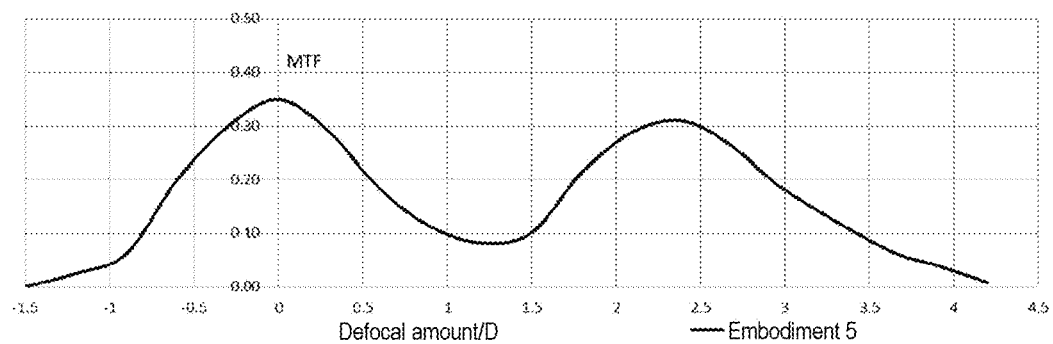
FIG. 11 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.12 and Table 1.13, wherein the refractive index of the material is 1.48, the diffraction bifocal design is adopted, the anterior surface is aspherical, the posterior surface comprises diffraction rings, the radius of the first diffraction ring is 0.65 mm, the height of the diffraction ring is 1.82 μm, the refractive power is 14.0D, the additional refractive power is +2.4D, the depth of field is 0.90D. Clear vision of the near vision distance corresponding to the add power above +3.30D can be realized. The through focus response curve at the frequency of 50 lp/mm and at 3 mm aperture is shown in FIG. 11. The MTF respectively has a peak at the far and near focal points, the minimum MTF between the peaks of the far and near focal points is above 0.05.

TABLE 1.12

Parameters of basal surface shape of example 5

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.48 | 20.0 | 16.50 | −11.10 | 0.73 | 0 | −9.926E−04 | −8.582E−05 | −1.675E−06 | 1.083E−06 | 0.9 | 1.06 | 2.4 | Anterior surface |

TABLE 1.13

Parameters of diffraction rings of example 5

| No. of diffraction ring | Radius of diffraction ring/mm | Height of diffraction ring/μm |
|---|---|---|
| 1 | 0.649496 | 1.82 |
| 2 | 0.92165 | 1.82 |
| 3 | 1.132706 | 1.82 |
| 4 | 1.312576 | 1.82 |
| 5 | 1.472826 | 1.82 |
| 6 | 1.619384 | 1.82 |
| 7 | 1.755773 | 1.82 |
| 8 | 1.884297 | 1.82 |
| 9 | 2.006563 | 1.82 |
| 10 | 2.123746 | 1.82 |

Example 6

Figure 12:
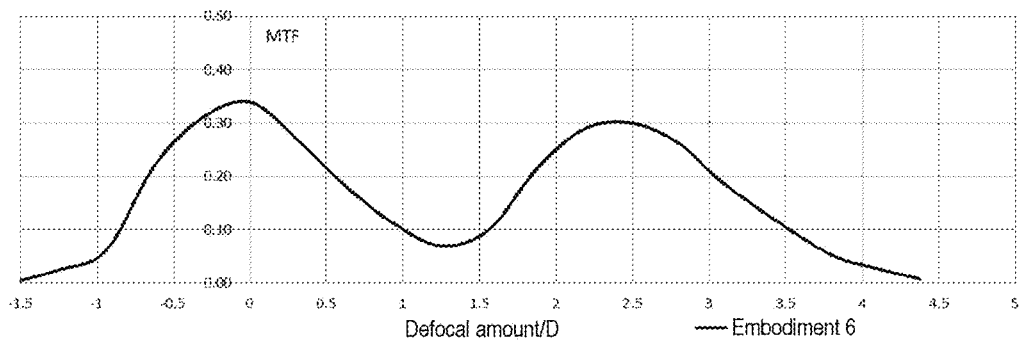
FIG. 12 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.14 and Table 1.15, wherein the refractive index of the material is 1.48, the diffraction bifocal design is adopted, the anterior surface is aspherical, the posterior surface comprises diffraction rings, the radius of the first diffraction ring is 0.64 mm, the height of the diffraction ring is 1.91 μm, the refractive power is 20.0D, the additional refractive power is +2.5D, the depth of field is 1.0D. Clear vision of the near vision distance corresponding to the add power above +3.50D can be realized. The through focus response curve at the frequency of 50 lp/mm and at 3 mm aperture is shown in FIG. 12. The MTF respectively has a peak at the far and near focal points, the minimum MTF between the peaks of the far and near focal points is above 0.05.

TABLE 1.14

Parameters of basal surface shape of example 6

| Refractive index | Refractive power | Ra | Rp | CT | Q | A4 | A6 | A8 | A10 | Depth of field | $\eta$ | Additional refractive power | Location of aspherical surface |
|---|---|---|---|---|---|---|---|---|---|---|---|---|---|
| 1.48 | 20.0 | 16.00 | −11.10 | 0.73 | 0 | −1.105E−03 | −1.061E−04 | −2.226E−06 | 1.399E−06 | 1.0 | 1.06 | 2.5 | Anterior surface |

TABLE 1.15

Parameters of diffraction rings of example 6

| No. of diffraction ring | Radius of diffraction ring/mm | Height of diffraction ring/μm |
|---|---|---|
| 1 | 0.636912 | 1.91 |
| 2 | 0.904025 | 1.91 |
| 3 | 1.111305 | 1.91 |
| 4 | 1.288042 | 1.91 |
| 5 | 1.445728 | 1.91 |
| 6 | 1.589723 | 1.91 |
| 7 | 1.724015 | 1.91 |
| 8 | 1.850523 | 1.91 |
| 9 | 1.971023 | 1.91 |
| 10 | 2.082513 | 1.91 |

Example 7

Figure 13:
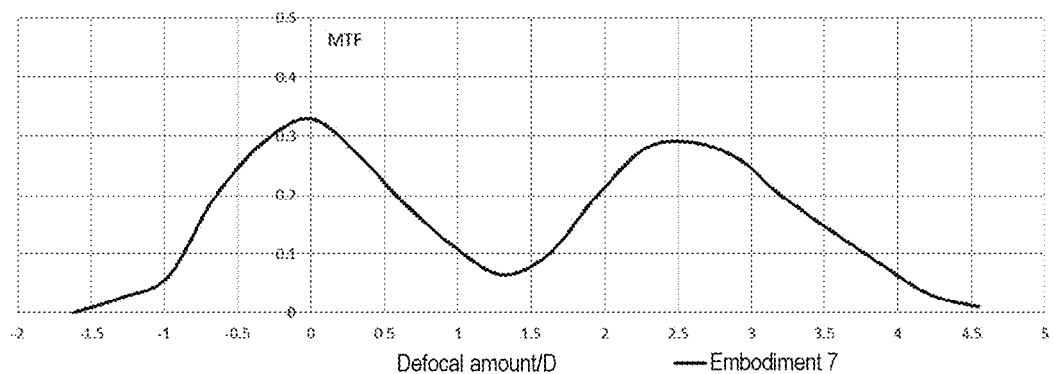
FIG. 13 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.16 and Table 1.17, wherein the refractive index of the material is 1.46, the diffraction bifocal design is adopted, the anterior surface is aspherical, the posterior surface comprises diffraction rings, the radius of the first diffraction ring is 0.62 mm, the height of the diffraction ring is 2.29 μm, the refractive power is 5.0D, the additional refractive power is +2.6D, the depth of field is 1.1D. Clear vision of the near vision distance corresponding to the add power above +3.70D can be realized. The through focus response curve at the frequency of 50 lp/mm and at 3 mm aperture is shown in FIG. 13. The MTF respectively has a peak at the far and near focal points, the minimum MTF between the peaks of the far and near focal points is above 0.05.

TABLE 1.16

Parameters of basal surface shape of example 7

| Refractive index | Refractive power | Ra | Rp | CT | Q | A4 | A6 | A8 | A10 | Depth of field | $\eta$ | Additional refractive power | Location of aspherical surface |
|---|---|---|---|---|---|---|---|---|---|---|---|---|---|
| 1.46 | 5.0 | 54.68 | −49.60 | 0.70 | −600.83 | −1.567E−03 | 3.366E−05 | 0 | 0 | 1.1 | 1.46 | 2.6 | Anterior surface |

TABLE 1.17

Parameters of diffraction rings of example 7

| No. of diffraction ring | Radius of diffraction ring/mm | Height of diffraction ring/μm |
|---|---|---|
| 1 | 0.624645 | 2.29 |
| 2 | 0.88604 | 2.29 |
| 3 | 1.088499 | 2.29 |
| 4 | 1.260816 | 2.29 |
| 5 | 1.414123 | 2.29 |
| 6 | 1.554124 | 2.29 |
| 7 | 1.684207 | 2.29 |
| 8 | 1.806583 | 2.29 |
| 9 | 1.922792 | 2.29 |
| 10 | 2.033958 | 2.29 |
| 11 | 2.140937 | 2.29 |

Example 8

Figure 14:
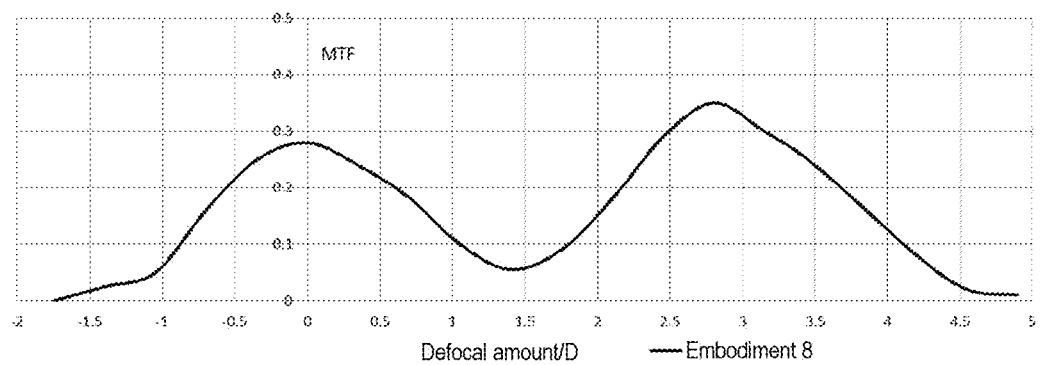
FIG. 14 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.18 and Table 1.19, wherein the refractive index of the material is 1.46, the diffraction bifocal design is adopted, the anterior surface is aspherical, the posterior surface comprises diffraction rings, the radius of the first diffraction ring is 0.60 mm, the height of the diffraction ring is 2.66 μm, the refractive power is 5.0D, the additional refractive power is +2.8D, the depth of field is 1.3D. Clear vision of the near vision distance corresponding to the add power above +4.10D can be realized. The through focus response curve at the frequency of 50 lp/mm and at 3 mm aperture is shown in FIG. 14. The MTF respectively has a peak at the far and near focal points, the minimum MTF between the peaks of the far and near focal points is above 0.05.

TABLE 1.18

Parameters of basal surface shape of example 8

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.46 | 5.0 | 60.04 | −49.60 | 0.70 | −2144.84 | −1.407E−03 | −9.871E−05 | 1.063E−05 | 0 | 1.3 | 1.93 | 2.8 | Anterior surface |

TABLE 1.19

Parameters of diffraction rings of example 8

| No. of diffraction ring | Radius of diffraction ring/mm | Height of diffraction ring/μm |
|---|---|---|
| 1 | 0.602449 | 2.66 |
| 2 | 0.854285 | 2.66 |
| 3 | 1.049142 | 2.66 |
| 4 | 1.214815 | 2.66 |
| 5 | 1.362047 | 2.66 |
| 6 | 1.496343 | 2.66 |
| 7 | 1.620972 | 2.66 |
| 8 | 1.738064 | 2.66 |
| 9 | 1.849101 | 2.66 |
| 10 | 1.955165 | 2.66 |
| 11 | 2.057076 | 2.66 |

Example 9

Figure 15:
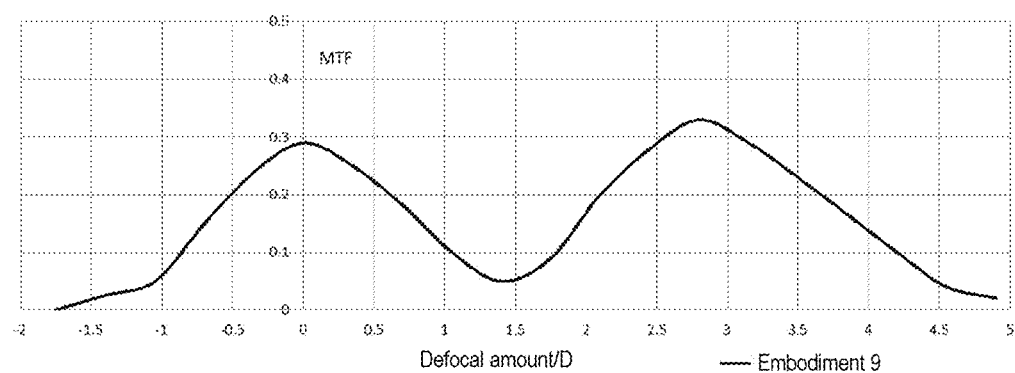
FIG. 15 shows a through focus response curve of an intraocular lens according to an embodiment of the first aspect of the present invention at a spatial frequency of 50 lp/mm and at a 3 mm aperture.

The parameters of the basal surface shape and the parameters of the diffraction ring are respectively shown in Table 1.20 and Table 1.21, wherein the refractive index of the material is 1.48, the diffraction bifocal design is adopted, the anterior surface is aspherical, the posterior surface comprises diffraction rings, the radius of the first diffraction ring is 0.60 mm, the height of the diffraction ring is 2.10 μm, the refractive power is 20.0D, the additional refractive power is +2.8D, the depth of field is 1.5D. Clear vision of the near vision distance corresponding to the add power above +4.30D can be realized. The through focus response curve at the frequency of 50 lp/mm and at 3 mm aperture is shown in FIG. 15. The MTF respectively has a peak at the far and near focal points, the minimum MTF between the peaks of the far and near focal points is above 0.05.

TABLE 1.20

Parameters of basal surface shape of example 9

| Refractive index | Refractive power | Ra | Rp | CT | Q | A4 | A6 | A8 | A10 | Depth of field | η | Additional refractive power | Location of aspherical surface |
|---|---|---|---|---|---|---|---|---|---|---|---|---|---|
| 1.48 | 20.0 | 15.0 | −11.10 | 0.73 | 0 | −7.053E−04 | −1.145E−04 | −4.849E−06 | 3.348E−06 | 1.5 | 1.06 | 2.8 | Anterior surface |

TABLE 1.21

Parameters of diffraction rings of example 9

| No. of diffraction ring | Radius of diffraction ring/mm | Height of diffraction ring/μm |
|---|---|---|
| 1 | 0.605367 | 2.40 |
| 2 | 0.858616 | 2.40 |
| 3 | 1.054709 | 2.40 |
| 4 | 1.221561 | 2.40 |
| 5 | 1.369963 | 2.40 |
| 6 | 1.505445 | 2.40 |
| 7 | 1.631293 | 2.40 |
| 8 | 1.74965 | 2.40 |
| 9 | 1.862009 | 2.40 |
| 10 | 1.969461 | 2.40 |

In summary, the intraocular lens according to the first aspect of the present invention is wherein the optical portion of the intraocular lens has an anterior and a posterior optical surfaces, one of which comprises an aspherical surface which assumes the function of depth of field extension and the other optical surface has a multifocal structure which assumes the function of providing two or more focal points, wherein the aspherical surface provides a depth of field which matches with the absolute value of the difference in refractive power of at least one pair of adjacent focal points of the two or more focal points provided by the multifocal structure. The aspherical surface, on the one hand, provides continuity of the focal points of the multifocal structure and, on the other hand, extends near vision in the direction of near focal point through the depth of field, thereby achieving continuous, uninterrupted full-range vision and adequate near vision. The intraocular lens of the first aspect of the present invention has a through focus response curve having a multi-peak structure at a spatial frequency of 50 lp/mm, with the absolute value of the difference in refractive power of at least one pair of adjacent peaks being greater than or equal to 1.6D, and the minimum value of MTF between the at least one pair of adjacent peaks being greater than or equal to 0.05, resulting in a continuous visual range.

Figure 16:
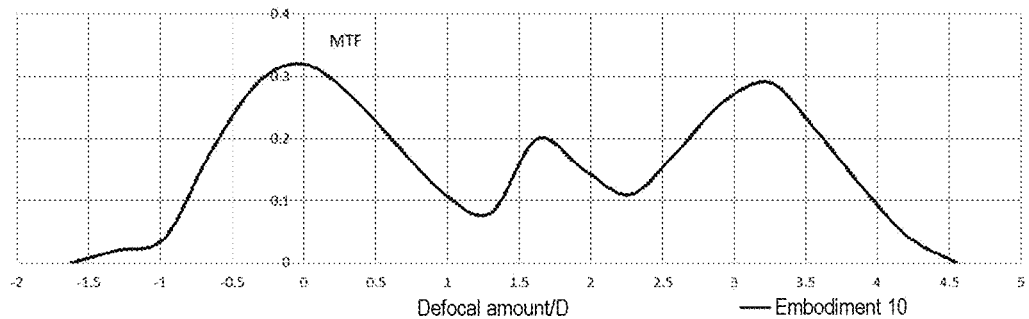
FIG. 16 shows a through focus response curve of an intraocular lens according to an embodiment of the first aspect of the present invention at a spatial frequency of 50 lp/mm and at a 3 mm aperture.

The inventive concept of the first aspect of the present invention may also be applied to intraocular lenses with more focal points, such as three focal points, four focal points, etc. Table 1.22 shows example 10 in which the concept of the first aspect of the present invention is implemented in a trifocal intraocular lens. In this example 10, the material had a refractive index of 1.48, the lens had a refractive power of 14.0D, the optical portion is of biconvex construction, a large depth of field aspherical surface is located on the anterior surface of the lens and diffractive rings are located on the posterior surface of the lens, seven diffractive rings are distributed over a 3 mm diameter, the first diffractive ring has a radius of 0.55 mm and the diffractive rings have heights alternating between 2.29/1.53 μm. The diffractive rings of the intraocular lens provide a near vision additional refractive power of +3.20D and an mid-range additional refractive power of +1.6D, and the aspherical surface of the intraocular lens provides a depth of field of 0.7D at a 3 mm aperture, thereby making the three focal points continuous with each other and extending the clear near vision distance to 3.90D. The through focus response curve at frequency of 50 lp/mm and at 3 mm aperture is shown in FIG. 16. The MTF has a peak at each of the far, middle and near focal points, with altogether three peaks, and the minimum of the MTF between adjacent peaks is above 0.05 and is close to 0.10.

TABLE 1.22

Parameters of basal surface shape of example 10

| Refractive index | Refractive power | Ra | Rp | CT | A6 | A8 | Depth of field | η | Mid-range additional refractive power | Near additional refractive power | Location of aspherical surface | Location of diffraction rings |
|---|---|---|---|---|---|---|---|---|---|---|---|---|
| 1.48 | 14.0 | 120.00 | −10.00 | 0.90 | −1.166E−03 | 1.677E−05 | 0.7 | 1.04 | 1.6 | 3.2 | Anterior surface | Posterior surface |

TABLE 1.23

Parameters of diffraction rings of example 10

| No. of diffraction ring | Radius of diffraction ring/mm | Height of diffraction ring/μm |
|---|---|---|
| 1 | 0.557484 | 2.29 |
| 2 | 0.790361 | 1.53 |
| 3 | 0.970434 | 2.29 |
| 4 | 1.123432 | 1.53 |
| 5 | 1.259306 | 2.29 |
| 6 | 1.38315 | 1.53 |
| 7 | 1.497991 | 2.29 |
| 8 | 1.605798 | 1.53 |
| 9 | 1.707944 | 2.29 |
| 10 | 1.805426 | 1.53 |
| 11 | 1.899003 | 2.29 |
| 12 | 1.989263 | 1.53 |

The Chinese patent applications 201510010026.9 and 201610993382.1 disclose a multifocal intraocular lens where a certain spherical aberration is imparted to the multifocal intraocular lens by means of an aspherical surface that shifts the light rays between the focal points, improving the mid-range vision of multifocal and trifocal intraocular lenses, but fails to completely connect the focal points, and the aspherical surface is a conventional aspherical surface, exhibiting spherical aberrations on the order of microns under large pupils, which can only achieve its intended purpose when the large pupil optical surface is fully used (e.g., >5.0 mm), but fails to function properly under normal pupil conditions. As described above, the aspherical surface of the first aspect of the present invention differs from the conventional aspherical surface in asphericity by one or more orders of magnitude, and can therefore extend the focal point under normal pupil conditions, and can completely connect focal points when designed in combination with the diffraction rings.

Technical Effects of the Examples

Figure 6:
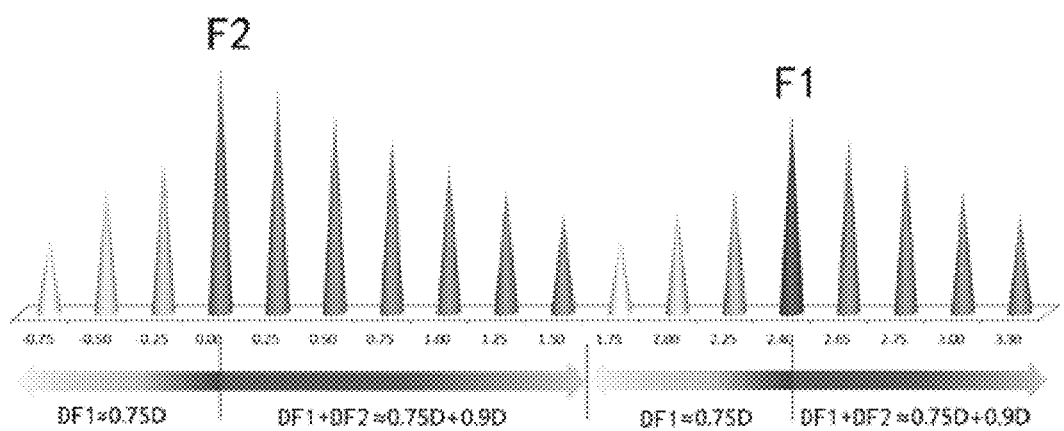
FIG. 6 schematically shows a continuous viewing range between two focal points of an intraocular lens according to an embodiment of the first aspect of the present invention.

Regarding example 5: the diffraction rings provide a refractive power of 20.0D and an additional refractive power of +2.4D, to which an aspherical surface capable of providing a depth of field of 0.9D is applied. With a human eye unilateral depth of field DF1 of 0.75D, the human eye unilateral depth of field DF1 at the far focal point F2+the depth of field DF2 provided by the aspherical surface+the human eye unilateral depth of field DF1 at the near focal point F1=2.4D. Therefore, the diffractive rings are designed to be +2.4D, so that the continuity of the visual range between the far focal point F2 and the near focal point F1 can be ensured, and the aspherical surface simultaneously achieves one-side depth of field extension for the near focal point F1, and vision can still be obtained inside the near focal point F1, as shown in FIG. 6.

The near vision limit that can be achieved with this example is:

multifocal additional refractive power (2.4D)+depth of field provided by aspherical surface (0.9D)+ human eye unilateral depth of field (0.75D)= 4.05D In fact, as the human eye unilateral depth of field at the near focal point side is insignificant due to low light energy, the near vision capable of obtaining clear vision is:

multifocal additional refractive power (2.4D)+depth of field provided by aspherical surface (0.9D)= 3.3D Thus, in this example, the intraocular lens achieves continuous and clear vision from infinity to +3.3D.

Figure 17:
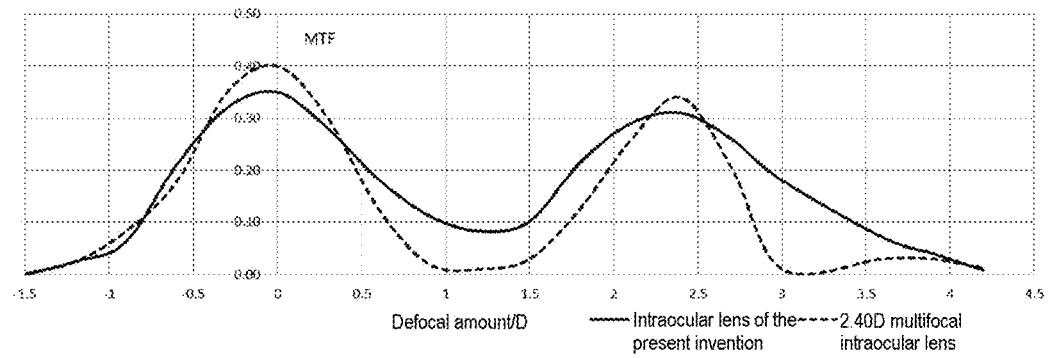
FIG. 17 shows the through focus response curves of an intraocular lens according to an embodiment of the first aspect of the present invention and a prior art +2.4D multifocal intraocular lens at a spatial frequency of 50 lp/mm and at a 3 mm aperture.

FIG. 17 shows the through focus response curves of an intraocular lens according to the first aspect of the present invention and a prior art +2.4D multifocal intraocular lens at a spatial frequency of 50 lp/mm. It can be seen that the intraocular lens of the first aspect of the present invention has a slightly reduced through focus response at both the far and near focal points due to the large depth of field of the aspherical surface, and that the through focus response increases in the near direction from the far focal point, in the far direction from the near focal point and between the two focal points. And in the direction inside the near focal point, the through focus response is also increased. The bifocal design of the diffraction ring structure enables the through focus response curve of the intraocular lens to have a double-peak structure, and the large-depth-of-field aspherical surface enables a situation that the MTF between two adjacent focal points of the intraocular lens is not less than 0.05, so that continuous visual range is realized.

Figure 18:
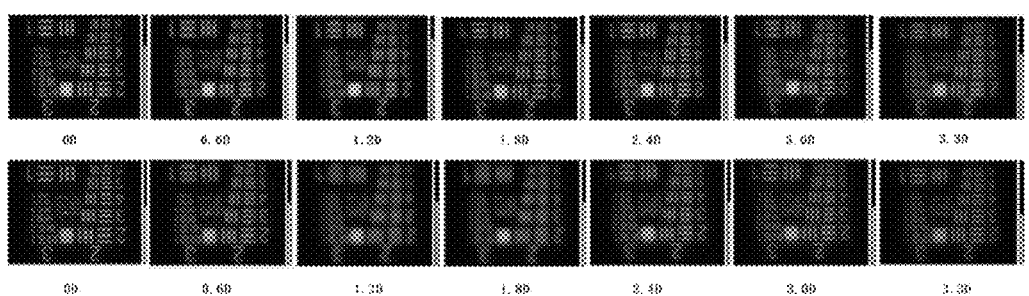
FIG. 18 shows American military standard full optotype measurements of an intraocular lens according to the first aspect of the present invention and a prior art +3.0D multifocal intraocular lens.

FIG. 18 shows American military standard full optotype measurements of an intraocular lens according to the first aspect of the present invention and a prior art +3.0D multifocal intraocular lens. In FIG. 18, the upper row of optotypes is the measurements of an intraocular lens according to the first aspect of the present invention and the lower row of optotypes is the measurements of a prior art +3.0D multifocal intraocular lens. It can be seen that although the diffractive rings only achieve an additional refractive power of +2.4D, the intraocular lens according to the first aspect of the present invention remains clear at the +3.3D additional refractive power and unlike the prior art multifocal intraocular lens, the vision of the intraocular lens according to the first aspect of the present invention is continuous.

Figure 19A:
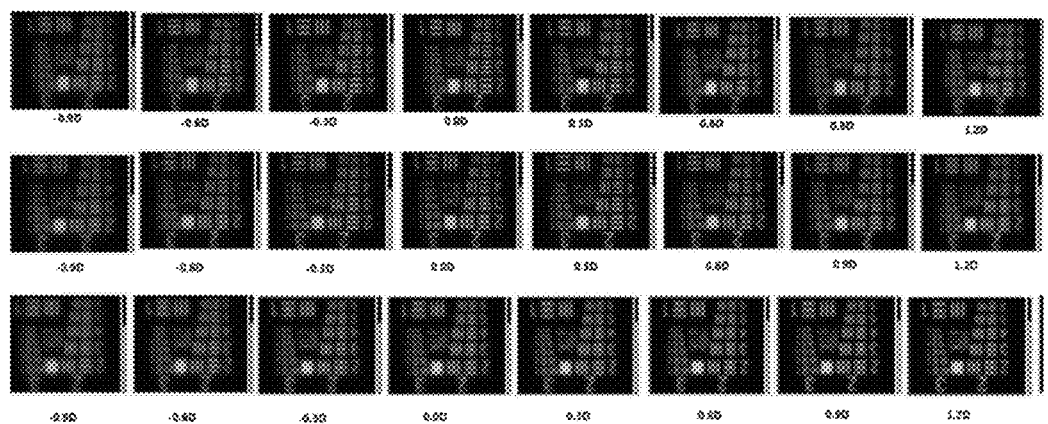
Figure 19B:
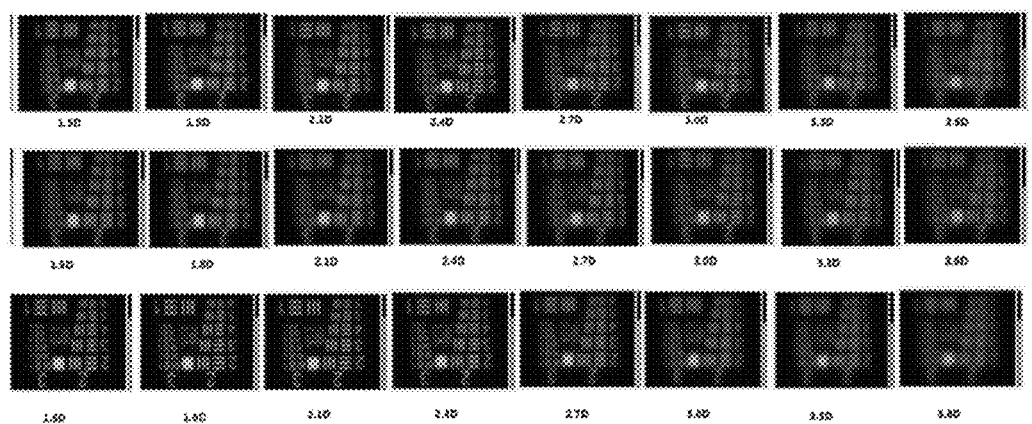

FIGS. 19a and 19b show a comparison of American military standard full optotype measurements of an intraocular lens according to the first aspect of the present invention with Symfony ZXR00 intraocular lens and a prior art trifocal intraocular lens. In FIG. 19a and FIG. 19b, the upper row of optotypes is the measurements of an intraocular lens according to the first aspect of the present invention, the middle row of optotypes is the measurements of a prior art trifocal intraocular lens, and the lower row of optotypes is the measurements of a Symfony ZXR00 intraocular lens. It can be seen that the Symfoni ZXR00 intraocular lens, although providing continuous vision, is deficient in near vision; the prior art trifocal intraocular lens can obtain far, middle and near vision with adequate near vision capability, but has discontinuous vision with breakpoints and dark images. The intraocular lens according to the first aspect of the present invention can obtain adequate near vision, has continuous vision without breakpoints, and has brighter images than that of the prior art trifocal intraocular lens.

The second aspect of the present invention is discussed in detail below. The artificial lens discussed in the second aspect of the present invention includes aphakic intraocular lens, phakic intraocular lens, and contact lens.

Figure 20:
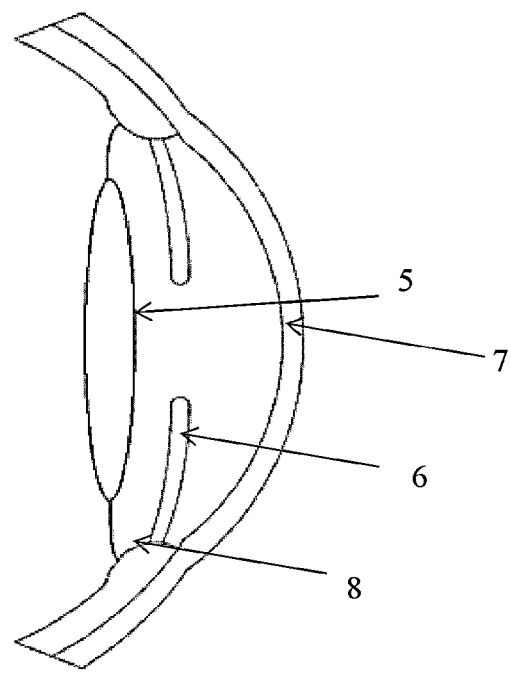
FIG. 20 shows a schematic view of an aphakic intraocular lens implanted within a human eye.

FIG. 20 shows a schematic view of an aphakic intraocular lens implanted within a human eye, wherein reference numeral 5 denotes the aphakic intraocular lens, reference numeral 6 denotes the iris, reference numeral 7 denotes the cornea, and reference numeral 8 denotes the ciliary sulcus.

Figure 21:
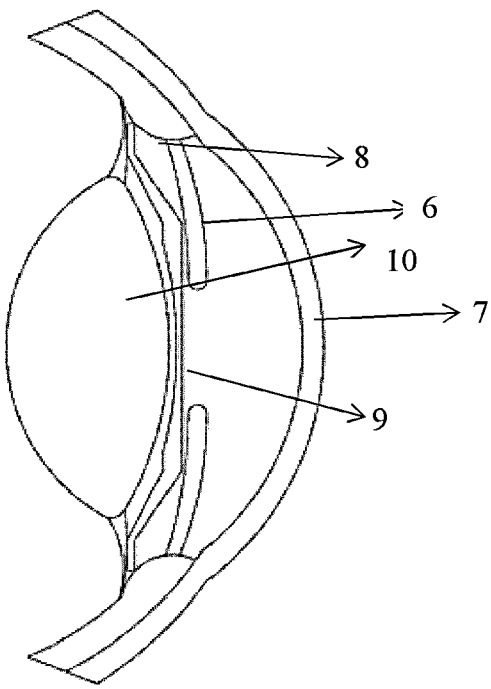
FIG. 21 shows a schematic view of a phakic intraocular lens implanted within a human eye.

FIG. 21 shows a schematic view of a phakic intraocular lens in a human eye, wherein reference numeral 9 denotes the phakic intraocular lens, reference numeral 6 denotes the iris, reference numeral 7 denotes the cornea, reference numeral 8 denotes the ciliary sulcus, and reference numeral 10 denotes the natural lens.

Figure 22:
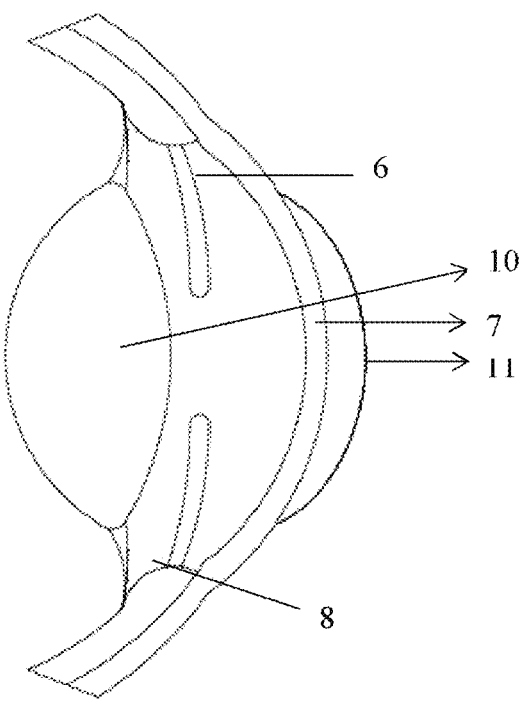
FIG. 22 shows a schematic view of a contact lens worn outside the human eye.

FIG. 22 shows a schematic view of a contact lens worn outside of a human eye, wherein reference numeral 11 denotes the contact lens, reference numeral 6 denotes the iris, reference numeral 7 denotes the cornea, reference numeral 8 denotes the ciliary sulcus, and reference numeral 10 denotes the natural lens.

The following embodiments are merely for further explanation of the second aspect of the present invention, but the second aspect of the present invention is not limited to the following embodiments. Any variations on these embodiments, which are within the principle, spirit and scope of the present invention, are intended to be within the scope of protection of the present invention.

Vision, i.e. visual resolving power, is the ability of the eye to distinguish the smallest distance between two object points outside the eye, and is usually measured by visual angle, the smaller the visual angle, the better the vision. Clinically, there are different expressions according to different visual charts. European and American countries usually use a fraction to represent the vision, with the numerator being the test distance and the denominator being the distance of an optotype from a tested eye when the optotype opens a 5' visual angle to the tested eye. For example, if the test distance is 20 ft, and the minimum optotype which can be clearly seen by the tested eye opens a 5' visual angle to the tested eye at a distance of 40 ft from the tested eye, then the fraction vision is 20/40; if the test distance is 6 μm, and the minimum optotype which can be clearly seen by the tested eye opens a 5' visual angle to the tested eye at a distance of 24 μm from the tested eye, then the fraction vision is 6/24. Decimal vision is a decimal form of the fraction vision. For example, if the fraction vision is 20/40, then the decimal vision is 0.5. The decimal vision can also be characterized by a reciprocal of a visual angle opened by the optotype at a standard test distance to the tested eye. For example, the optotype is ½, i.e. 0.5, when the minimum optotype which can be clearly seen by the tested eye at the standard test distance opens a visual angle of 2' to the tested eye. The 5-score recording method is to firstly determine a visual angle opened by an optotype at a standard test distance to the tested eye MAR (i.e. the reciprocal of the decimal vision), and then calculate the common logarithm of the visual angle 1 g MAR, and then subtract the 1 g MAR of the optotype from 5. For example, the reciprocal of a 0.5 optotype is 2, and 1 g2=0.3, and 5 minus 0.3 equals to 4.7. The second aspect of the present invention is discussed by taking the "rolling E" optotype and decimal record VA as an example.

Decimal record VA expresses vision in the reciprocal of the visual angle:

$$VA = \frac{1}{\alpha}$$

the visual angle is expressed in units of arc minutes, i.e., (1/60°), so that a VA value of 0.5 corresponds to a visual angle of:

$$2 \text{ arc minutes} = \left(\frac{2}{60}\right)°$$

Figure 23:
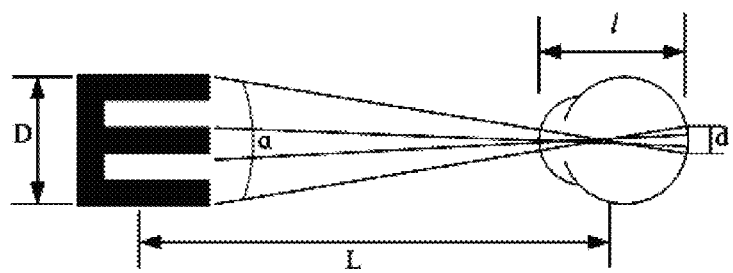
FIG. 23 shows an optotype, viewing angles and a human eye.

The "rolling E" optotype is shown as "E" in FIG. 23. The sizes of "E" are different for different visions. For far vision, the distance between the eyes and the optotype is 6 μm, and the height of the optotype can be calculated as:

$$D = L \times \tan\alpha = 6 \text{ m} \times \tan\left(\frac{2}{60}\right)° \approx 3.49 \text{ mm}$$

Assuming that the length of the axis of the eye is 24 mm, the height of the optotype imaged in the eye can be calculated as:

$$d = l \times \tan\left(\frac{2}{60}\right)° \approx 24 \text{ mm} \times \tan\left(\frac{2}{60}\right)° \approx 0.014 \text{ mm}$$

The height of the optotype imaged in the eyes is the limit that a person with far vision of 0.5 VA can distinguish.

MTF of an artificial lens can be determined by placing the artificial lens in a human eye model, forming an optical system with the human eye model, detecting and simulating the MTF of the artificial lens eye. In principle and structure, the imaging process of this optical system is the same as the imaging process of a distant object in the artificial lens eye, therefore the MTF of the artificial lens in the human eye model can represent the optical quality of the human eye after the IOL is implanted. The spatial cut-off frequency of the MTF can represent the resolution limit of the human eye.

Figure 24:
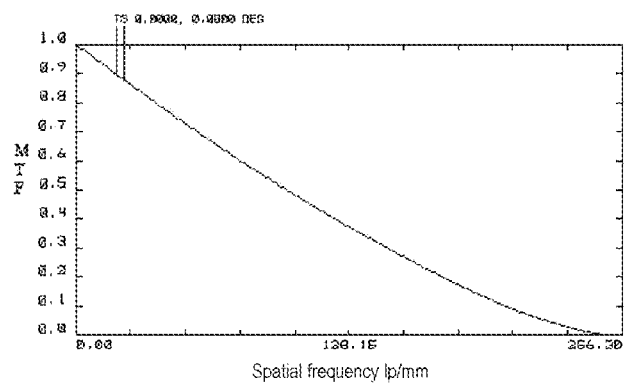
FIG. 24 shows a typical MTF.

A typical MTF curve is shown in FIG. 24, where the intersection point of the MTF curve and the abscissa is the resolution limit of the optical system, which is also called the spatial cut-off frequency. The spatial frequency is given in lp/mm, i.e. the number of line pairs per millimeter that can be resolved.

The resolution limit d≈0.014 mm of the human eye with a vision 0.5 VA is converted into the spatial frequency, so that the spatial cut-off frequency of the human eye is expressed as follows under the condition of far vision:

$$f_j = \frac{1}{d} \approx \frac{1}{0.014} \approx 71.62 \text{ lp/mm}$$

Figure 25:
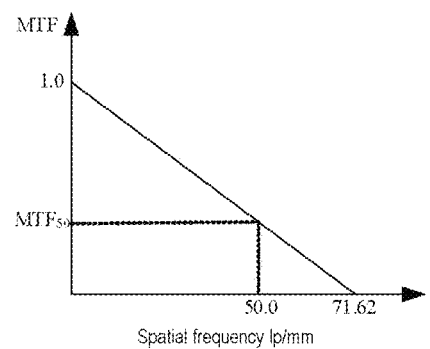
FIG. 25 shows a MTF for a human eye with 0.5 VA far vision.

Then, the MTF curve for a human eye with a far vision of 0.5 VA is shown in FIG. 25.

In addition to the above-mentioned method for calculating the resolution limit d and the spatial cut-off frequency $f_j$ of the human eye, there are other calculation methods. For example, the resolution limit of the human eye can also be characterized by the minimum resolution angle, which is expressed as $$d = \frac{1.22\lambda}{D},$$

where λ represents the wavelength and D represents the pupil diameter of the human eye. The spatial cut-off frequency can be expressed as $$f_j = \frac{\alpha}{d},$$

where α represents the viewing angle.

From the relationship of similar triangles in FIG. 25, the $MTF_{50}$ at a spatial frequency of 50 lp/mm can be calculated as:

$$MTF_{50} = \frac{71.62 - 50}{71.62} \approx 0.30$$

Therefore, the MTF of the artificial lens in the human eye model reaches more than 0.30 at the spatial frequency of 50 lp/mm, and the requirement for far vision of 0.5 VA can be met.

By performing calculations in a similar way, the MTFs of the artificial lens in the human eye model satisfying far visions of 0.8 VA, 1.0 VA, 1.2 VA and 1.5 VA respectively are shown in Table 2.1.

TABLE 2.1

MTFs of the artificial lens in the human eye model satisfying various visions

| Vision | Resolution limit (mm) | Spatial cut-off frequency (lp/mm) | MTF at 50 lp/mm | MTF at 100 lp/mm |
|---|---|---|---|---|
| 0.5  | 0.0139 | 71.94  | 0.30 | 0    |
| 0.6  | 0.0116 | 86.21  | 0.42 | 0    |
| 0.7  | 0.0100 | 100.00 | 0.50 | 0    |
| 0.8  | 0.0087 | 114.94 | 0.56 | 0.13 |
| 0.9  | 0.0078 | 128.21 | 0.61 | 0.22 |
| 0.97 | 0.0072 | 138.89 | 0.64 | 0.28 |
| 1.0  | 0.0069 | 144.92 | 0.65 | 0.31 |
| 1.1  | 0.0063 | 158.73 | 0.68 | 0.37 |
| 1.2  | 0.0058 | 172.41 | 0.71 | 0.42 |
| 1.3  | 0.0054 | 185.19 | 0.73 | 0.46 |
| 1.4  | 0.0050 | 200.00 | 0.75 | 0.50 |
| 1.5  | 0.0046 | 217.39 | 0.77 | 0.54 |

The MTFs of the artificial lens in the human eye model satisfying various visions are calculated schematically as above. The second aspect of the present invention is not limited to the above calculation method. Various vision representations and the relation between the vision and the spatial frequency curve may requires different calculation methods, and all the calculation methods, as long as they are in conformity with the principle, spirit and scope of the present invention, will fall within the protection scope of the present invention. For example, when the MTF at the spatial frequency f is calculated based on the relationship of similar triangles shown in FIG. 25, it is considered that the MTF and the spatial frequency have a linear relationship. However, the MTF and the spatial frequency usually have a nonlinear relationship, and a general expression for the MTF is MTP (f)=$a_0+a_1 f+a_2 f^2+ \ldots a_n f^n$, where $a_0, a_1, a_2, \ldots a_n$ are polynomial coefficients. Assuming that a quadratic nonlinear relationship is present between the MTF and the spatial frequency, that is, MTF(f)=$a_0+a_2 f^2$. Assuming that the spatial cut-off frequency is F, then MTF(F)=0. The MTF has a value of 1 at the spatial frequency of 0, that is, MTF(0)=1. Then, $a_0=1$ and $$a_2 = -\frac{1}{F^2}.$$

Hence, the MTF at any spatial frequency is given by $$MTF(f) = -\frac{f^2}{F^2} + 1,$$

where MTF(f) and the spatial cut-off frequency exhibit a quadratic nonlinear relationship. In practice, the MTFs at certain spatial frequencies need to be determined according to specific MTF curves.

In the above illustrative calculations of the MTF of an artificial lens in a human eye model satisfying various visions, the spatial frequency is expressed in units of lp/mm, i.e., the number of line pairs per millimeter. The spatial frequency can also be expressed as the number of cycles per millimeter c/mm or mm$^{-1}$. In some ophthalmic instruments, the unit of spatial frequency is c/d or cpd, i.e., cycle/degree, which refers to the number of cycles that a bright and dark stripe appears repeatedly per one degree of viewing angle. Taking the human eye as an example, assuming that the distance between the object and the image plane is 17 mm, the conversion relationship between c/d and c/mm is approximately: c/d=0.297 c/mm. In actual calculations, proper conversion is required according to specific parameters.

The monofocal artificial lenses in the prior arts are aimed to allow the artificial lens to reach the diffraction limit, namely the highest MTF. Typically, the MTF is greater than or equal to 0.43 and can frequently goes up to 0.50 or more. Clinically, after the monofocal artificial lens is implanted or worn, the vision reaches to a value of greater than or equal to 0.8 VA and the patients are satisfied. When the MTF of the artificial lens exceeds 0.31 or even 0.42 at 100 lp/mm, the resolution is excessive and cannot be definitely perceived by human eyes.

Based on this, the second aspect of the present invention provides an aspherical artificial lens, which has an aspherical design and makes use of the excessive resolution to reasonably disperse the focal points of the artificial lens and provides a longer depth of field. The artificial lens of the second aspect of the present invention has an MTF between 0 and 0.42, preferably between 0.13 and 0.37, more preferably between 0.13 and 0.28 at a spatial resolution of 100 lp/mm in a standard human eye model at a 3 mm aperture. After implantation, a far vision of 0.8 VA-1.2 VA and a certain of mid-range vision can be obtained. Aspherical surface is commonly used in ophthalmic lens and is mainly used for correcting spherical aberration of the artificial lens eye, so that human eyes can still obtain excellent imaging quality under the condition of large pupils at night. The expression of the curve of the aspherical surface on the plane rZ of the two-dimensional coordinate system is as follows:

$$z(r) = \frac{\frac{1}{R} * r^2}{1 + \left(1 - (1+Q) * \left(\frac{1}{R}\right)^2 * r^2\right)^{\frac{1}{2}}} + \sum_{i=m}^{n} A_{2i} * r^{2i}$$

wherein R is the radius of curvature of the basal spherical surface of the aspherical surface, r is the perpendicular distance from a point on the curve to the abscissa axis (Z), $A_{2i}$ is aspherical high-order term coefficient, m and n are both integers not less than 1 and n>m, Q is aspherical coefficient, wherein points on the aspherical surface are obtained in a way that the curve rotates about the abscissa axis (Z) for symmetry variation.

The aspherical surface is defined by a scale factor η of the equivalent radius of curvature, the scale factor η being a ratio of the equivalent radii of curvature $\overline{R}$ of the aspherical surface at different positions m, n of the curve on the plane rZ of the two-dimensional coordinate system:

$$\eta = \frac{\overline{R}_m}{\overline{R}_n}$$

wherein the equivalent radius of curvature $\overline{R}$ is expressed as:

$$\overline{R} = \frac{r^2 + z^2}{2 \cdot z}$$

where r is the perpendicular distance from a point on the curve to the abscissa axis Z, i.e., the height difference between the point and the vertex of the aspherical surface, and z is the perpendicular distance from the point on the curve to the ordinate axis r.

In the second aspect of the present invention, the asphericity of the intraocular lens is characterized by the scale factor η of the equivalent radius of curvature of the aspherical surface at r=1.5 mm, $\overline{R}_{1.5}$ and the equivalent radius of curvature at r=1.0 mm, $\overline{R}_{1.0}$, namely:

$$\eta = \frac{\overline{R}_{1.5}}{\overline{R}_{1.0}}$$

In the second aspect of the present invention, the defocal amount of the artificial lens is characterized by an absolute value of the difference in refractive power |ΔD| at r=1.5 mm and r=1.0 mm.

Figure 26:
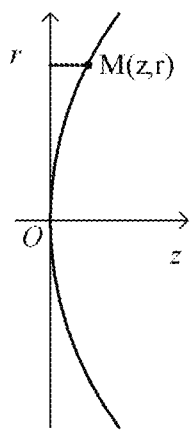
FIG. 26 shows an aspherical surface curve and its coordinate system according to the second aspect of the present invention.

The surface shape of the aspherical surface is characterized by the difference in height of the aspherical surface at r=1.5 mm and r=1.0 mm, namely:

$$\Delta Z = Z(r=1.5) - Z(r=1.0)$$

wherein ΔZ is the difference in height of the aspherical surface; Z(r=1.5) is the height of the aspherical surface at a perpendicular distance of 1.5 mm from the abscissa axis Z; Z(r=1.0) is the height of the aspherical surface at a perpendicular distance of 1.0 mm from the abscissa axis Z. FIG. 26 shows an surface shape of an aspherical surface, an rZ coordinate system and a point M thereon according to the second aspect of the present invention.

Table 2.2 shows some embodiments of an artificial lens according to the second aspect of the present invention embodied as an aphakic intraocular lens and the MTF at 100 lp/mm and at 3 mm aperture in a standard human eye model, wherein the aspherical surface is located at the anterior surface of the optical portion of the aphakic intraocular lens. It will be readily understood by those skilled in the art that the aspherical surface may also be located at the posterior surface of the aphakic intraocular lens, or both the anterior and posterior surfaces may be aspheric. Some embodiments with the aspherical surface located at the posterior surface of the aphakic intraocular lens are schematically shown in Table 2.3. In Table 2.2, $Q_a$, $A_{4a}$, $A_{6a}$ and $A_{8a}$ represent aspherical coefficients of the anterior surface of the aphakic intraocular lens. In Table 2.3, $Q_p$, $A_{4p}$, $A_{6p}$ and $A_{8p}$ represent the aspherical coefficients of the posterior surface of the aphakic intraocular lens. In the embodiments shown in Table 2.2, some of the embodiments employ coefficients Q, $A_{4a}$, $A_{6a}$, and some of the embodiments additionally employ an aspherical coefficient $A_{8a}$. It is readily understood by those skilled in the art that any suitable combination of aspherical coefficients can be selectively used in the expression of the aspherical surface to realize the second aspect of the present invention. In the following, subscript "a" in a symbol indicates that said symbol corresponds to the anterior surface, and subscript "p" in a symbol indicates that said symbol corresponds to the posterior surface.

Table 2.2 schematically lists examples of the aphakic intraocular lenses having a higher refractive index and a lower refractive index and with various refractive powers and various surface shapes.

TABLE 2.2

Some embodiments of an aphakic intraocular lens according to the second aspect of the present invention

| Refractive index | Refractive power | Ra | Rp | d | Qa | $A_{4a}$ | $A_{6a}$ | $A_{8a}$ | MTF at 100 lp/mm | Δz | η | ΔD |
|---|---|---|---|---|---|---|---|---|---|---|---|---|
| 1.46 | 5 | 51.39 | −49.57 | 0.8 | 246.613 | 1.5340E−03 | 1.7962E−04 | 0 | 0.13 | 0.021 | 0.80 | 1.68 |
| | 5 | 86.97 | −45.50 | 0.8 | 492.230 | −4.5354E−03 | 1.7641E−04 | 0 | 0.13 | 0.005 | 10.00 | −1.97 |
| | 20 | 13.94 | −11.10 | 2.0 | 13.761 | 1.1223E−03 | 1.1194E−04 | 0 | 0.13 | 0.054 | 0.93 | 1.61 |
| | 20 | 15.38 | −11.10 | 2.0 | −15.877 | −4.3186E−03 | 1.9219E−04 | 0 | 0.13 | 0.023 | 1.23 | −2.27 |
| | 36 | 4.95 | −11.10 | 2.0 | 0.950 | 1.1106E−03 | −1.4174E−04 | 0 | 0.13 | 0.138 | 0.98 | 1.38 |
| | 36 | 4.94 | −11.10 | 2.0 | −2.183 | −3.4241E−03 | 1.6527E−04 | 0 | 0.13 | 0.110 | 1.06 | −2.19 |
| | 5 | 56.35 | −45.50 | 0.8 | −5142.327 | 2.8892E−03 | −1.5159E−04 | 0 | 0.28 | 0.016 | 0.84 | 1.00 |
| | 5 | 69.91 | −45.50 | 0.8 | 442.250 | −3.3433E−03 | 8.9772E−05 | 0 | 0.28 | 0.004 | 8.28 | −1.67 |
| | 20 | 8.89 | −20.00 | 2.0 | 3.432 | 7.7850E−04 | 4.6385E−05 | 0 | 0.28 | 0.077 | 0.97 | 1.19 |
| | 20 | 14.79 | −11.10 | 2.0 | 3.788 | −4.1753E−03 | 1.5589E−04 | 0 | 0.28 | 0.028 | 1.17 | −1.90 |
| | 36 | 6.80 | −6.80 | 2.0 | 1.947 | 2.8178E−04 | −1.1264E−04 | 0 | 0.28 | 0.097 | 0.99 | 1.02 |
| | 36 | 4.88 | −11.10 | 2.0 | −1.135 | −3.4421E−03 | 1.2266E−04 | 0 | 0.28 | 0.115 | 1.05 | −1.75 |
| | 5 | 61.62 | −45.50 | 0.6 | 90.499 | 8.0446E−04 | 2.0517E−05 | 1.1163E−07 | 0.37 | 0.014 | 0.89 | 0.60 |
| | 5 | 78.45 | −45.50 | 0.6 | 836.070 | −2.3351E−03 | −3.1415E−05 | | 0.37 | 0.003 | 2.75 | −1.34 |
| | 20 | 8.23 | −25.00 | 0.8 | 1.946 | 6.3064E−04 | 2.7134E−05 | 0 | 0.37 | 0.082 | 0.98 | 0.93 |
| | 20 | 14.49 | −11.10 | 0.8 | 6.999 | −3.6581E−03 | 1.0349E−04 | 0 | 0.37 | 0.031 | 1.14 | −1.64 |
| | 36 | 4.88 | −11.10 | 2.0 | −0.954 | 1.7543E−03 | 4.9990E−05 | 0 | 0.37 | 0.138 | 0.99 | 1.30 |
| | 36 | 4.86 | −11.10 | 2.0 | −0.919 | −3.2493E−03 | 9.9543E−05 | 0 | 0.37 | 0.117 | 1.05 | −1.56 |
| | 5 | 56.35 | −45.50 | 0.8 | −1808.319 | 1.3256E−03 | −8.8884E−06 | 0 | 0.42 | 0.013 | 0.92 | 0.50 |
| | 5 | 75.49 | −45.50 | 0.8 | 763.449 | −2.0329E−003 | −4.3802E−005 | 0 | 0.42 | 0.004 | 1.98 | −1.19 |
| | 20 | 12.44 | −12.37 | 0.8 | 4.136 | 4.5406E−04 | 9.4278E−06 | 0 | 0.42 | 0.054 | 0.98 | 0.59 |
| | 20 | 14.35 | −11.10 | 0.8 | 9.455 | −3.1325E−03 | 6.1313E−05 | 0 | 0.42 | 0.033 | 1.11 | −1.36 |
| | 36 | 4.88 | −11.10 | 2.0 | 0.279 | 3.8693E−04 | −7.1539E−05 | 0 | 0.42 | 0.135 | 0.99 | 1.05 |
| | 36 | 4.85 | −11.10 | 2.0 | −0.781 | −3.0880E−03 | 8.2435E−05 | 0 | 0.42 | 0.118 | 1.04 | −1.42 |
| 1.55 | 5 | 111.79 | −111.79 | 0.5 | −16781.36 | −1.6277E−03 | −9.9601E−05 | 1.4692E−05 | 0.13 | 0.006 | 5.00 | −2.05 |
| | 5 | 1553.92 | −45.50 | 0.5 | 333029.100 | 1.1672E−03 | 2.5502E−04 | −2.6821E−05 | 0.13 | 0.007 | 0.50 | 2.14 |
| | 20 | 430.40 | −11.10 | 0.7 | 21490.920 | 1.0669E−03 | 1.7026E−04 | −1.5817E−05 | 0.13 | 0.007 | 0.56 | 2.37 |
| | 20 | 22.65 | −22.65 | 0.7 | −88.249 | −1.1602E−03 | −6.8133E−05 | 1.0649E−05 | 0.13 | 0.019 | 1.15 | −2.08 |
| | 36 | 12.59 | −11.10 | 1.0 | 10.508 | 6.7589E−04 | 1.6710E−04 | −1.1017E−05 | 0.13 | 0.057 | 0.95 | 2.49 |
| | 36 | 12.75 | −12.75 | 1.0 | −20.226 | −1.6009E−03 | −8.8428E−05 | 1.7623E−05 | 0.13 | 0.038 | 1.10 | −2.70 |
| | 5 | 1565.76 | −45.50 | 0.5 | 186205.200 | 7.0401E−04 | 2.1719E−04 | −3.1472E−05 | 0.28 | 0.005 | 0.46 | 1.35 |
| | 5 | 94.94 | −94.94 | 0.5 | −7285.473 | −1.0956E−03 | −7.4614E−05 | 9.1946E−06 | 0.28 | 0.005 | 2.79 | −1.73 |
| | 20 | 21.64 | −21.64 | 0.7 | 36.435 | 4.7232E−04 | 1.0740E−04 | −1.4785E−05 | 0.28 | 0.034 | 0.94 | 1.44 |

TABLE 2.2-continued

Some embodiments of an aphakic intraocular lens according to the second aspect of the present invention

| Refractive index | Refractive power | Ra | Rp | d | Qa | $A_{4a}$ | $A_{6a}$ | $A_{8a}$ | MTF at 100 lp/mm | $\Delta z$ | $\eta$ | $\Delta D$ |
|---|---|---|---|---|---|---|---|---|---|---|---|---|
| | 20 | 22.65 | −22.65 | 0.7 | −88.249 | −1.1602E−03 | −6.8133E−05 | 1.0649E−05 | 0.28 | 0.019 | 1.15 | −2.08 |
| | 36 | 12.32 | −12.32 | 1.0 | −19.582 | −1.2061E−03 | −7.6640E−05 | 1.3025E−05 | 0.28 | 0.041 | 1.09 | −2.34 |
| | 36 | 12.60 | −11.10 | 1.0 | 6.758 | 4.2936E−04 | 1.0104E−04 | −1.0682E−05 | 0.28 | 0.054 | 0.97 | 1.54 |
| | 5 | 89.66 | −89.66 | 0.5 | −5297.661 | −7.7375E−04 | −5.6463E−05 | 5.9096E−06 | 0.37 | 0.004 | 1.71 | −1.34 |
| | 5 | 1525.86 | −45.50 | 0.5 | 335411.800 | 3.6553E−04 | 2.0756E−04 | −3.4786E−05 | 0.37 | 0.003 | 0.48 | 0.88 |
| | 20 | 22.16 | −22.16 | 0.7 | −81.025 | −8.1735E−04 | −5.9490E−05 | 7.6891E−06 | 0.37 | 0.021 | 1.11 | −1.72 |
| | 20 | 452.64 | −11.10 | 0.7 | 2094.773 | 5.0032E−04 | 7.3079E−05 | −1.0187E−05 | 0.37 | 0.004 | 0.67 | 0.86 |
| | 36 | 11.79 | −11.82 | 1.0 | 4.026 | 3.2179E−04 | 7.3757E−05 | −9.0358E−06 | 0.37 | 0.057 | 0.98 | 1.15 |
| | 36 | 12.18 | 12.18 | 1.0 | −15.894 | −1.0871E−03 | −7.2210E−05 | 1.1292E−05 | 0.37 | 0.043 | 1.07 | −2.09 |
| | 5 | 89.54 | −89.54 | 0.5 | −3871.691 | −6.7196E−04 | −4.8446E−05 | 4.8366E−06 | 0.42 | 0.005 | 1.51 | −1.20 |
| | 5 | 1445.02 | −45.50 | 0.5 | 184701.300 | 1.3137E−04 | 2.1791E−04 | −3.8595E−05 | 0.42 | 0.002 | 0.44 | 0.61 |
| | 20 | 22.10 | −22.10 | 0.7 | −57.810 | −8.0155E−04 | −5.1634E−05 | 6.7472E−06 | 0.42 | 0.022 | 1.10 | −1.53 |
| | 20 | 459.97 | −11.10 | 0.7 | −593.439 | 3.6741E−04 | 4.9765E−05 | −7.4024E−06 | 0.42 | 0.002 | 0.72 | 0.64 |
| | 36 | 11.79 | −11.82 | 1.0 | 3.300 | 2.5634E−04 | 5.8430E−05 | −7.6774E−06 | 0.42 | 0.056 | 0.98 | 0.96 |
| | 36 | 12.13 | −12.13 | 1.0 | −15.601 | −9.7149E−04 | −7.1424E−05 | 1.0424E−05 | 0.42 | 0.043 | 1.07 | −1.97 |

TABLE 2.3

Some embodiments of an aphakic intraocular lens according to the second aspect of the present invention

| Refractive index | Refractive power | Ra | Rp | d | Qp | $A_{4p}$ | $A_{6p}$ | $A_{8p}$ | MTF at 100 lp/mm | $\Delta z$ | $\eta$ | $\Delta D$ |
|---|---|---|---|---|---|---|---|---|---|---|---|---|
| 1.46 | 5 | 49.56 | −49.72 | 0.8 | 162.112916 | −1.458254E−003 | −1.426908E−004 | −6.34612E−006 | 0.28 | 0.021 | 0.81 | 1.53 |
| | 5 | 49.56 | −50.98 | 0.8 | 23.468183 | −1.262065E−003 | −1.032385E−004 | −5.38762E−007 | 0.37 | 0.019 | 0.85 | 1.11 |

According to some embodiments of the second aspect of the present invention, the aphakic intraocular lens has an MTF at 100 lp/mm and at a 3 mm aperture in a Liou standard human eye model of 0 to 0.42, preferably 0.13 to 0.37; more preferably 0.13 to 0.28. The standard human eye model adopted by the second aspect of the present invention is a Liou aspherical human eye model, and the parameters are shown in Table 2.4.

TABLE 2.4

Liou aspherical human eye model

| Parameter | Radius/ mm | Aspherical coefficient | Thickness/ mm | Refractive index |
|---|---|---|---|---|
| Cornea anterior surface | 7.77 | −0.18 | 0.5 | 1.376 |
| Cornea posterior surface | 6.40 | −0.60 | | |

The parameters of the human eye model used in the method of the second aspect of the present invention are not limited to the parameters shown in Table 2.4. Any variations of parameters, while being in conformity with the principle, spirit and scope of the present invention, will still fall within the scope of protection of the present invention.

According to some embodiments of the second aspect of the present invention, the difference in height $\Delta Z$ of the aspherical surface of the aphakic intraocular lens at 3 mm and 2 mm apertures is 0.002-0.138 mm, preferably 0.003-0.138 mm; more preferably 0.004 to 0.138 mm. According to some embodiments of the second aspect of the present invention, the aphakic intraocular lens has an asphericity scale factor $\eta$ at 3 mm and 2 mm apertures of 0.44 to 10.00, preferably 0.46 to 10.00. According to some embodiments of the second aspect of the present invention, the aphakic intraocular lens has an asphericity scale factor $\eta$ at 3 mm and 2 mm apertures of 0.44 to 0.99, preferably 0.46 to 0.99. The refractive power of the aphakic intraocular lens is detected in water and under the condition of normal use, the detecting diameter is less than or equal to 4.0 mm, preferably less than or equal to 3.5 mm, and more preferably less than or equal to 3.0 mm. The aphakic intraocular lens according to the second aspect of the present invention can achieve an adequate defocal amount. According to some embodiments of the second aspect of the present invention, the absolute value of the difference in refractive power $|\Delta D|$ of the aphakic intraocular lens at r=1.5 mm and r=1.0 mm is greater than or equal to 0.50D; preferably, $|\Delta D|$ is 0.60D-2.70D; more preferably, $|\Delta D|$ is 1.00D-2.70D. According to some embodiments of the second aspect of the present invention, the difference in refractive power $\Delta D$ of the aphakic intraocular lens at r=1.5 mm and r=1.0 mm is greater than or equal to 0.50D, preferably, $\Delta D$ is 0.60D-2.49D, more preferably, $\Delta D$ is 1.00D-2.49D.

Table 2.5 shows some embodiments of the artificial lens according to the second aspect of the present invention embodied as a phakic intraocular lens and the MTF at 100 lp/mm and at a 3 mm aperture in a phakic human eye model.

TABLE 2.5

Some embodiments of the phakic intraocular lens according to the second aspect of the present invention

| Refractive index | Refractive power | Ra | Rp | d | Qp | $A_{4p}$ | $A_{6p}$ | MTF at 100 lp/mm | Δz | η | ΔD |
|---|---|---|---|---|---|---|---|---|---|---|---|
| 1.46 | −5 | Infinity | 24.5 | 0.1 | 71.431 | −2.4556E−03 | −3.2775E−04 | 0.13 | 0.015 | 1.23 | 1.99 |
| | −5 | Infinity | 24.2 | 0.1 | 140.299 | 1.3401E−003 | 4.9100E−004 | 0.13 | 0.044 | 0.79 | −4.04 |
| | −20 | Infinity | 6.2 | 0.1 | −9.775 | 1.7365E−03 | −2.5327E−04 | 0.13 | 0.091 | 1.05 | 1.47 |
| | −25 | Infinity | 5.0 | 0.1 | 4.069 | −2.7702E−03 | −2.4604E−03 | 0.13 | 0.118 | 1.05 | 3.06 |
| | −25 | Infinity | 4.9 | 0.1 | 2.304 | −1.2680E−04 | 2.5489E−04 | 0.13 | 0.146 | 0.96 | −3.98 |
| | −5 | Infinity | 24.5 | 0.1 | −126.536 | −5.5363E−04 | −2.0515E−04 | 0.28 | 0.018 | 1.16 | 1.40 |
| | −5 | Infinity | 25.0 | 0.1 | 140.102 | 1.3362E−03 | 3.7119E−04 | 0.28 | 0.039 | 0.83 | −2.82 |
| | −20 | Infinity | 6.2 | 0.1 | −9.364 | 2.2734E−03 | −1.8690E−04 | 0.28 | 0.094 | 1.03 | 0.88 |
| | −25 | Infinity | 4.7 | 0.1 | 2.862 | −2.3587E−03 | −1.4266E−03 | 0.28 | 0.134 | 1.02 | 0.84 |
| | −25 | Infinity | 4.8 | 0.1 | 0.336 | −3.3060E−04 | 7.2196E−04 | 0.28 | 0.142 | 0.97 | −3.18 |
| | −5 | Infinity | 24.5 | 0.1 | 40.623 | −1.5938E−03 | −1.3409E−04 | 0.37 | 0.019 | 1.12 | 1.14 |
| | −5 | Infinity | 25.3 | 0.1 | 84.850 | 1.3260E−03 | 2.9434E−04 | 0.37 | 0.036 | 0.85 | −2.32 |
| | −20 | Infinity | 6.2 | 0.1 | −9.339 | 2.8083E−03 | −1.7150E−04 | 0.37 | 0.096 | 1.02 | 0.49 |
| | −25 | Infinity | 5.0 | 0.1 | 2.972 | −1.5533E−03 | −1.4209E−03 | 0.37 | 0.126 | 1.02 | 1.19 |
| | −25 | Infinity | 4.9 | 0.1 | 0.199 | 4.3585E−04 | 1.0006E−04 | 0.37 | 0.135 | 0.99 | −1.55 |
| | −5 | Infinity | 24.5 | 0.1 | 49.523 | −1.4794E−03 | −1.2731E−04 | 0.42 | 0.020 | 1.10 | 0.98 |
| | −5 | Infinity | 25.7 | 0.1 | 61.303 | 1.3674E−03 | 2.1536E−04 | 0.42 | 0.034 | 0.87 | −1.88 |
| | −25 | Infinity | 4.9 | 0.1 | −0.067 | 1.3855E−04 | 1.6702E−05 | 0.42 | 0.131 | 1.00 | −0.88 |
| 1.55 | −5 | Infinity | 42.8 | 0.1 | 243.054 | −1.3856E−03 | −2.1717E−04 | 0.13 | 0.009 | 1.23 | 2.02 |
| | −5 | Infinity | 42.8 | 0.1 | 388.284 | 9.4583E−04 | 2.8610E−04 | 0.13 | 0.025 | 0.79 | −3.81 |
| | −20 | Infinity | 10.7 | 0.1 | −1.100 | −9.4714E−04 | −1.7966E−04 | 0.13 | 0.053 | 1.05 | 1.96 |
| | −25 | Infinity | 8.56 | 0.1 | −1.124 | −6.8824E−04 | −2.8324E−04 | 0.13 | 0.067 | 1.04 | 2.23 |
| | −25 | Infinity | 8.56 | 0.1 | −0.695 | 1.5384E−03 | 3.9459E−04 | 0.13 | 0.084 | 0.95 | −3.87 |
| | −5 | Infinity | 42.8 | 0.1 | 271.698 | −1.1441E−03 | −1.9348E−04 | 0.28 | 0.010 | 1.16 | 1.53 |
| | −5 | Infinity | 42.8 | 0.1 | 289.452 | 7.2521E−04 | 2.3334E−04 | 0.28 | 0.022 | 0.83 | −2.79 |
| | −20 | Infinity | 10.7 | 0.1 | 14.562 | −1.8564E−03 | −3.9555E−04 | 0.28 | 0.055 | 1.03 | 1.56 |
| | −25 | Infinity | 8.56 | 0.1 | 12.740 | −2.0883E−03 | −8.8769E−04 | 0.28 | 0.070 | 1.03 | 1.70 |
| | −25 | Infinity | 8.56 | 0.1 | 0.809 | 9.6917E−04 | 2.3698E−04 | 0.28 | 0.081 | 0.96 | −2.76 |
| | −5 | Infinity | 42.8 | 0.1 | 280.241 | −9.7918E−04 | −1.8065E−04 | 0.37 | 0.011 | 1.12 | 1.25 |
| | −5 | Infinity | 42.8 | 0.1 | 0.809 | 9.6917E−04 | 2.3698E−04 | 0.37 | 0.021 | 0.86 | −2.29 |
| | −20 | Infinity | 10.7 | 0.1 | 14.892 | −1.6115E−03 | −3.8344E−04 | 0.37 | 0.056 | 1.02 | 1.15 |
| | −25 | Infinity | 8.56 | 0.1 | 12.921 | −1.6160E−03 | −8.8115E−04 | 0.37 | 0.072 | 1.01 | 1.04 |
| | −25 | Infinity | 8.56 | 0.1 | −660.035 | 1.7830E−03 | 1.2950E−04 | 0.37 | 0.077 | 0.98 | −1.47 |
| | −5 | Infinity | 42.8 | 0.1 | 283.464 | −8.8784E−04 | −1.7467E−04 | 0.42 | 0.012 | 1.11 | 1.11 |
| | −5 | Infinity | 42.8 | 0.1 | −660.035 | 1.7830E−03 | 1.2950E−04 | 0.42 | 0.020 | 0.87 | −2.02 |
| | −20 | Infinity | 10.7 | 0.1 | 15.072 | −1.3919E−03 | −3.7682E−04 | 0.42 | 0.057 | 1.02 | 0.84 |
| | −25 | Infinity | 8.56 | 0.1 | −24.260 | 4.4893E−03 | −2.5745E−04 | 0.42 | 0.075 | 0.99 | −0.82 |

According to the second aspect of the present invention, MTF is the result of placing a phakic intraocular lens in a phakic human eye model, wherein the phakic human eye model is an intraocular lens model formed by adding 20.0D to the Liou standard human eye model, and parameters of the model are shown in Table 2.6, wherein Ra, Rp are the radii of curvature of the anterior and posterior surfaces, respectively, d is the center thickness, n is the refractive index, Q, $A_4$ and $A_6$ are aspherical coefficients, and the aspherical surface is located on the anterior surface of the phakic intraocular lens.

TABLE 2.6

Parameters of the phakic intraocular lens model

| Ra | Rp | d | n | Q | $A_4$ | $A_6$ |
|---|---|---|---|---|---|---|
| 16.356 | −16.356 | 0.8 | 1.50 | −6.893 | −3.953e−04 | −5.507e−06 |

The phakic intraocular lens shown in Table 2.5 is in the form of an anterior-plano-posterior-concave surface, with the aspherical surface located on the posterior surface, i.e., the concave surface of the intraocular lens. As will be readily understood by those skilled in the art, the phakic intraocular lens may be biconcave, anterior-convex-posterior-concave, anterior-plano-posterior-concave, and the like. The aspherical surface may also be located on the anterior surface of the phakic intraocular lens, or both the anterior and posterior surfaces may be aspherical. Some embodiments are schematically shown in Table 2.7. The embodiments shown in Table 2.7 employ aspherical coefficients Q, $A_4$, $A_6$ and $A_8$. Those skilled in the art will readily appreciate that any suitable combination of aspherical coefficients can be selectively used in the expression of the aspherical surface to realize the second aspect of the present invention.

TABLE 2.7

Some embodiments of the phakic intraocular lens according to the second aspect of the present invention

| Refractive index | Refractive power | Ra | Rp | d | Qa | $A_{4a}$ | $A_{6a}$ | $A_{8a}$ | MTF at 100 lp/mm | $\Delta z$ | $\eta$ | $\Delta D$ |
|---|---|---|---|---|---|---|---|---|---|---|---|---|
| 1.43 | −5 | −30.59 | 37.60 | 0.1 | 247.926633 | −9.822644E−004 | −3.862985E−004 | −1.424615E−004 | 0.28 | 0.04 | 0.74 | −3.73 |
| | −5 | 46.82 | 14.00 | 0.1 | 569.43 | 1.793797E−003 | 2.422149E−005 | −8.675554E−005 | 0.28 | 0.023 | 0.82 | 0.98 |
| | −25 | −7.52 | 7.52 | 0.1 | −7.493714 | 2.999354E−03 | −3.573936E−04 | 3.893262E−05 | 0.13 | 0.067 | 1.09 | 1.42 |
| | −25 | −7.40 | 7.52 | 0.1 | 4.924696 | −3.784559E−04 | −1.087143E−03 | 1.105767E−04 | 0.13 | 0.103 | 0.92 | −3.17 |

In Chinese patent application CN201510441713.6, an aspherical phakic intraocular lens is proposed, in which the absolute value of the peripheral equivalent radius of curvature is greater than the central equivalent radius of curvature, for realizing myopic peripheral defocus and controlling development of myopia. The second aspect of the present invention differs from this patent application in that the aspherical working region of the second aspect of the present invention is a small aperture used daily, preferably an aperture with a diameter of 3.5 mm, and more preferably an aperture with a diameter of 3.0 mm, so it is necessary to achieve a sharp refractive power change in the small aperture, while Chinese patent application CN201510441713.6 is aimed to achieve peripheral defocus control while peripheral defocus generally acts on a large aperture with a diameter of 4 mm or more, and the refractive power distribution tends to be flat in order to avoid resolution reduction.

According to some embodiments of the second aspect of the present invention, the MTF of the phakic intraocular lens in the artificial lens eye model at 100 lp/mm and at a 3 mm aperture is 0 to 0.42, preferably 0.13 to 0.37, more preferably 0.13 to 0.28.

According to some embodiments of the second aspect of the present invention, the difference $\Delta Z$ in height of the aspherical surface of the phakic intraocular lens at 3 mm and 2 mm apertures is 0.009-0.146 mm.

According to some embodiments of the second aspect of the present invention, the phakic intraocular lens has an asphericity scale factor $\eta$ at 3 mm and 2 mm apertures of 0.74 to 1.23.

According to some embodiments of the second aspect of the present invention, the phakic intraocular lens has an asphericity scale factor $\eta$ at 3 mm and 2 mm apertures of 1.01 to 1.23.

The refractive power of the phakic intraocular lens is detected in water and under the condition of normal use, the detecting diameter is preferably less than or equal to 3.5 mm, and more preferably less than or equal to 3.0 mm. The phakic intraocular lens according to the second aspect of the present invention can achieve an adequate defocal amount. According to some embodiments of the second aspect of the present invention, the absolute value of the difference in refractive power $|\Delta D|$ of the phakic intraocular lens at 3 mm and 2 mm apertures is greater than or equal to 0.50D; preferably, $|\Delta D|$ is 0.50D-4.04D; more preferably, $|\Delta D|$ is 0.84D-4.04D. According to some embodiments of the second aspect of the present invention, the difference in refractive power $\Delta D$ of the aphakic intraocular lens at 3 mm and 2 mm apertures is greater than or equal to 0.50D, preferably, $\Delta D$ is 0.50D-3.06D, more preferably, $\Delta D$ is 1.01D-3.06D.

Table 2.8 shows some examples of the artificial lens according to the second aspect of the present invention embodied as a contact lens and the MTF of the contact lens positioned on the corneal surface of the above phakic human eye model at 100 lp/mm and at 3 mm aperture, wherein the aspherical surface is located on the anterior and/or posterior surfaces of the contact lens. In the embodiment shown in Table 2.8, coefficients Q, $A_4$, $A_6$ and $A_8$ are used. Those skilled in the art will readily appreciate that any suitable combination of aspherical coefficients can be selectively used in the expression of the aspherical surface to realize the second aspect of the present invention.

TABLE 2.8

Some embodiments of the contact lens according to the second aspect of the present invention

| Refractive index | Refractive power | Rp/mm | Qp | Ra | CT | Qa | $A_{4a}$ | $A_{6a}$ | $A_{8a}$ | MTF (100 lp/mm) | $\Delta z$ | $\Delta D$ | $\eta$ |
|---|---|---|---|---|---|---|---|---|---|---|---|---|---|
| 1.38 | 10.0 | 8.4 | 0 | 6.90 | 0.27 | 0.67 | 2.8845E−04 | 2.9600E−05 | −5.7513E−06 | 0.13 | 0.0946 | 1.445 | 0.990 |
| | 10.0 | 8.4 | 0 | 6.93 | 0.27 | −0.50 | −2.4210E−04 | −4.0379E−05 | 1.5607E−06 | 0.28 | 0.0896 | −0.893 | 1.009 |
| | 10.0 | 8.4 | 0 | 6.91 | 0.27 | 0.32 | 1.3509E−04 | 9.7152E−06 | −1.7429E−06 | 0.37 | 0.0931 | 0.808 | 0.995 |
| | 10.0 | 8.4 | 0 | 6.93 | 0.27 | −0.33 | −1.7391E−04 | −2.8927E−05 | 1.8233E−06 | 0.42 | 0.0903 | −0.524 | 1.006 |
| | 0.0 | 8.4 | −0.1 | 8.36 | 0.07 | 1.23 | 2.6303E−04 | 9.1435E−05 | −1.9305E−05 | 0.13 | 0.0783 | 1.342 | 0.987 |
| | 0.0 | 8.4 | −0.1 | 8.38 | 0.07 | −0.91 | −2.6450E−04 | −4.6631E−06 | −2.2326E−06 | 0.28 | 0.0735 | −0.949 | 1.010 |
| | 0.0 | 8.4 | −0.1 | 8.37 | 0.07 | 0.54 | 9.0886E−05 | 6.3603E−05 | −1.1359E−05 | 0.37 | 0.0768 | 0.687 | 0.994 |
| | 0.0 | 8.4 | −0.1 | 8.37 | 0.07 | 0.38 | 5.4887E−05 | 5.7309E−05 | −9.9086E−06 | 0.42 | 0.0765 | 0.538 | 0.995 |
| | −3.0 | 8.9 | −0.6 | 9.59 | 0.07 | −1.83 | −3.2581E−04 | −4.7403E−05 | 7.0446E−07 | 0.13 | 0.0629 | −1.381 | 1.018 |
| | −3.0 | 8.9 | −0.6 | 9.56 | 0.07 | 1.09 | 1.4454E−04 | 1.5628E−05 | −2.7189E−06 | 0.28 | 0.0673 | 0.810 | 0.992 |
| | −3.0 | 8.9 | −0.6 | 9.56 | 0.07 | 0.82 | 9.8785E−05 | 1.0940E−05 | −1.8033E−06 | 0.37 | 0.0669 | 0.627 | 0.994 |
| | −3.0 | 8.9 | −0.6 | 9.59 | 0.07 | −0.77 | −2.3204E−04 | −2.6367E−05 | 1.6705E−06 | 0.42 | 0.0642 | −0.696 | 1.010 |
| | −20.0 | 8.4 | −0.5 | 14.99 | 0.07 | 7.60 | 2.8175E−04 | 2.9349E−05 | −5.8568E−06 | 0.13 | 0.0443 | 1.118 | 0.978 |
| | −20.0 | 8.4 | −0.5 | 15.13 | 0.07 | −5.89 | −3.1302E−04 | −4.4131E−05 | 6.5998E−07 | 0.13 | 0.0389 | −1.515 | 1.026 |
| | −20.0 | 8.4 | −0.5 | 15.05 | 0.07 | 5.32 | 1.5942E−04 | 1.8294E−05 | −3.1302E−06 | 0.28 | 0.0433 | 0.668 | 0.986 |
| | −20.0 | 8.4 | −0.5 | 15.12 | 0.07 | −3.09 | −2.2111E−04 | −2.8005E−05 | 1.5538E−06 | 0.37 | 0.0399 | −0.974 | 1.016 |
| | −20.0 | 8.4 | −0.5 | 15.12 | 0.07 | −2.33 | −1.9454E−04 | −2.3860E−05 | 1.5599E−06 | 0.42 | 0.0401 | −0.834 | 1.013 |
| 1.44 | 10.0 | 8.9 | −0.2 | 7.43 | 0.27 | 0.70 | 2.3768E−04 | 2.4155E−05 | −4.7495E−06 | 0.13 | 0.0874 | 1.429 | 0.991 |
| | 10.0 | 8.9 | −0.2 | 7.44 | 0.27 | 0.44 | 1.3407E−04 | 1.4311E−05 | −2.4751E−06 | 0.28 | 0.0864 | 0.978 | 0.995 |

TABLE 2.8-continued

Some embodiments of the contact lens according to the second aspect of the present invention

| Refractive index | Refractive power | Rp/mm | Qp | Ra | CT | Qa | $A_{4a}$ | $A_{6a}$ | $A_{8a}$ | MTF (100 lp/mm) | $\Delta z$ | $\Delta D$ | $\eta$ |
|---|---|---|---|---|---|---|---|---|---|---|---|---|---|
| | 10.0 | 8.9 | −0.2 | 7.46 | 0.27 | −0.45 | −1.9727E−04 | −2.6757E−05 | 1.3365E−06 | 0.37 | 0.0834 | −0.675 | 1.007 |
| | 10.0 | 8.9 | −0.2 | 7.45 | 0.27 | 0.25 | 6.2929E−05 | 6.7687E−06 | −1.1007E−06 | 0.42 | 0.0858 | 0.649 | 0.997 |
| | 0.0 | 8.9 | −0.4 | 8.87 | 0.07 | 1.32 | 2.4032E−04 | 4.1577E−05 | −1.0703E−05 | 0.13 | 0.0734 | 1.322 | 0.989 |
| | 0.0 | 8.9 | −0.4 | 8.88 | 0.07 | 0.79 | 1.3479E−04 | 2.4601E−05 | −5.5789E−06 | 0.28 | 0.0724 | 0.858 | 0.993 |
| | 0.0 | 8.9 | −0.4 | 8.89 | 0.07 | −0.92 | −1.6830E−04 | −3.5853E−05 | 4.0132E−06 | 0.37 | 0.0694 | −0.810 | 1.009 |
| | 0.0 | 8.9 | −0.4 | 8.88 | 0.07 | 0.42 | 6.3648E−05 | 1.2375E−05 | −2.5687E−06 | 0.42 | 0.0717 | 0.522 | 0.997 |
| | −3.0 | 8.4 | −0.3 | 8.88 | 0.07 | 1.48 | 2.8325E−04 | 2.9466E−05 | −5.6547E−06 | 0.13 | 0.0736 | 1.266 | 0.987 |
| | −3.0 | 8.4 | −0.3 | 8.90 | 0.07 | 0.97 | 1.6382E−04 | 1.8201E−05 | −3.0094E−06 | 0.28 | 0.0725 | 0.786 | 0.992 |
| | −3.0 | 8.4 | −0.3 | 8.93 | 0.07 | −0.68 | −2.4041E−04 | −2.8035E−05 | 1.3569E−06 | 0.37 | 0.0690 | −0.839 | 1.010 |
| | −3.0 | 8.4 | −0.3 | 8.91 | 0.07 | 0.73 | 5.4339E−05 | 9.9737E−06 | −1.5232E−06 | 0.42 | 0.0717 | 0.500 | 0.995 |
| | −20.0 | 8.9 | −0.8 | 14.90 | 0.07 | 5.81 | 2.1915E−04 | 2.3141E−05 | −4.6408E−06 | 0.13 | 0.0441 | 1.125 | 0.983 |
| | −20.0 | 8.9 | −0.8 | 14.94 | 0.07 | 3.73 | 1.1709E−04 | 1.3757E−05 | −2.3722E−06 | 0.28 | 0.0431 | 0.676 | 0.990 |
| | −20.0 | 8.9 | −0.8 | 15.00 | 0.07 | −3.70 | −2.0652E−04 | −2.5459E−05 | 1.4490E−06 | 0.37 | 0.0402 | −0.966 | 1.016 |
| | −20.0 | 8.9 | −0.8 | 15.00 | 0.07 | −3.04 | −1.8379E−04 | −2.1912E−05 | 1.4653E−06 | 0.42 | 0.0404 | −0.825 | 1.013 |

According to some embodiments of the second aspect of the present invention, the MTF of a contact lens in a human eye model at 100 lp/mm and at 3 mm aperture is 0-0.42, preferably 0.13-0.37, more preferably 0.13-0.28.

According to some embodiments of the second aspect of the present invention, the difference $\Delta Z$ in height of the aspherical surface of the contact lens at 3 mm and 2 mm apertures is 0.0389-0.0946 mm.

According to some embodiments of the second aspect of the present invention, the difference $\Delta Z$ in height of the aspherical surface of the contact lens at 3 mm and 2 mm apertures is 0.0431-0.0946 mm.

According to some embodiments of the second aspect of the present invention, the contact lens has an asphericity scale factor $\eta$ at 3 mm and 2 mm apertures of 0.978 to 1.026.

According to some embodiments of the second aspect of the present invention, the contact lens has an asphericity scale factor $\eta$ at 3 mm and 2 mm apertures of 0.978 to 0.99.

The refractive power of the contact lens is measured in air and under the condition of normal use, the detecting diameter is less than or equal to 4.0 mm, preferably less than or equal to 3.5 mm, and more preferably less than or equal to 3.0 mm. The contact lens according to the second aspect of the present invention can achieve an adequate defocal amount. According to some embodiments of the second aspect of the present invention, the absolute value of the difference in refractive power $|\Delta D|$ of the contact lens at r=1.5 mm and r=1.0 mm is greater than or equal to 0.50D; preferably, $|\Delta D|$ is 0.50D-1.515D; more preferably, $|\Delta D|$ is 0.627D-1.515D. According to some embodiments of the second aspect of the present invention, the difference in refractive power $\Delta D$ of the contact lens at r=1.5 mm and r=1.0 mm is greater than or equal to 0.50D, preferably, $\Delta D$ is 0.50D-1.445D, more preferably, $\Delta D$ is 0.627D-1.445D.

In order to use excessive resolution for focal extension, the artificial lens according to the second aspect of the present invention adopts an aspherical surface having a large asphericity at the center of the optical portion, which is called a focal extension zone. If the extent of the focal extension zone is too large, an excessively steep aspherical surface will give a large amount of aberrations to the artificial lens. It is therefore preferable that the optical portion of the artificial lens according to the second aspect of the present invention comprises three zones, wherein the central zone is a focal extension zone which is spanned within a diameter of less than or equal to 4.0 mm, preferably less than or equal to 3.5 mm, more preferably less than or equal to 3.0 mm of the artificial lens, the anterior surface and/or posterior surface of the focal extension zone being aspherical; the outermost zone is an aberration correction zone which is an annular region and serves for aberration modification and correction; a transition zone is located between the focal extension zone and the aberration correction zone, the transition zone is an annular region, and the width of the transition zone is greater than or equal to 0.25 mm, preferably 0.25-2.0 mm, and more preferably 0.25-1.0 mm. In some embodiments, the transition zone may be a combination of a plurality of annular regions.

In the artificial lens according to the second aspect of the present invention, the focal extension zone can provide a large change in refractive power to satisfy the requirements of the human eyes for far, mid-range and near vision. The aberration correction zone can provide the artificial lens with excellent imaging quality in dim environment or for large pupils. The transition zone can provide a smooth transition of the refractive power of the artificial lens to prevent image jump caused by abrupt change of the refractive power, and allow the surface of the artificial lens to assume a smooth optical surface.

Tables 2.9, 2.10 and 2.11 show some embodiments of the intraocular lens according to the second aspect of the present invention embodied as an aphakic intraocular lens, a phakic intraocular lens and a contact lens. The optical portion of the artificial lens of the second aspect of the present invention can be divided into three zones, namely, a focal extension zone at the center, an annular transition zone outside the focal extension zone, and an annular aberration correction zone outside the transition zone, wherein the radius of curvature of the anterior surface of the focal extension zone is $Ra_1$, the radius of curvature of the anterior surface of the transition zone is $Ra_2$, and the radius of curvature of the anterior surface of the aberration correction zone is $Ra_3$. The radii of curvature of the posterior surfaces of the focal extension zone, the transition zone and the aberration correction zone are the same and are all Rp, and Qp is an aspherical coefficient of the posterior surface. The anterior surfaces of the focal extension zone, the transition zone, and the aberration correction zone are aspherical having respective aspherical coefficients Q, $A_4$ and $A_6$. CT is the center thickness of the optical portion of the artificial lens.

Figure 30:
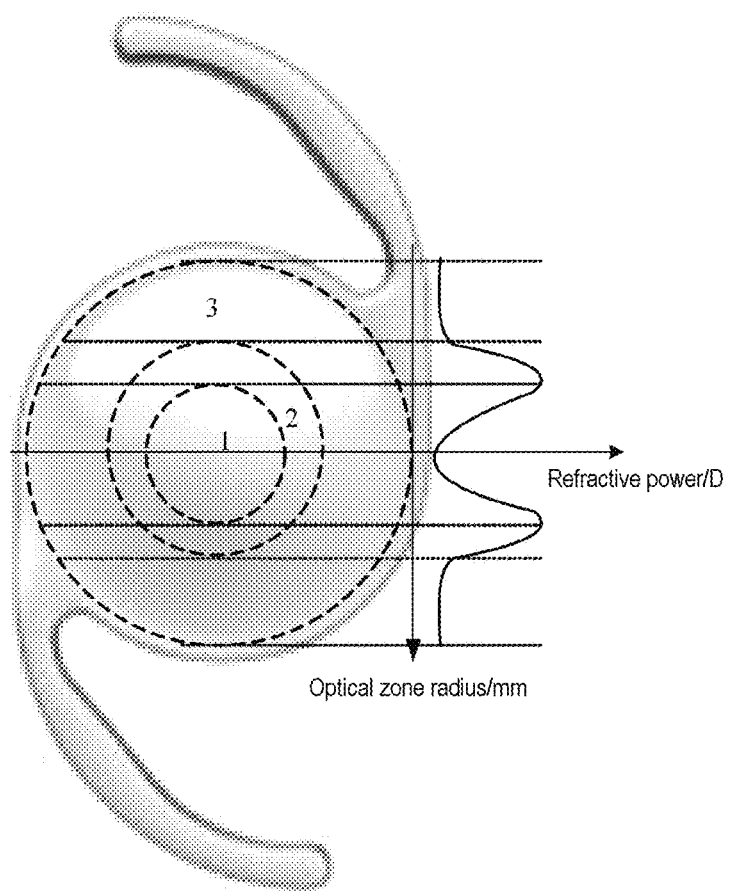
FIG. 30 shows a three zone design of an aphakic intraocular lens according to the second aspect of the present invention and an exemplary refractive power distribution thereof.

Taking an aphakic intraocular lens as an example, FIG. 30 shows a structural view of an aphakic intraocular lens having an optical portion divided into the above three zones and a refractive power distribution curve thereof over the optical portion. The aphakic intraocular lens shown in FIG. 30 includes a focal extension zone 1, a transition zone 2, and an aberration correction zone 3.

TABLE 2.9

Some embodiments of an artificial lens according to the second aspect of the present invention embodied as an aphakic intraocular lens

| Refractive power/D | Refractive index | Rp | Focal extension zone | | | | | | Transition zone |
|---|---|---|---|---|---|---|---|---|---|
| | | | Ra1 | CT | Diameter | Qa | $A_{4a}$ | $A_{6a}$ | Width |
| 5.0 | 1.46 | −45.5 | 53.30 | 0.55 | 2.00 | 173.95 | 1.026E−03 | 6.262E−05 | 0.25 |
| 9.0 | 1.46 | −45.5 | 20.00 | 0.62 | 2.00 | 21.65 | 9.268E−04 | 4.056E−05 | 1.00 |
| 14.0 | 1.46 | −19.5 | 16.16 | 0.70 | 2.00 | 7.45 | 8.688E−04 | 6.143E−05 | 2.00 |
| 30.0 | 1.46 | −11.1 | 6.48 | 1.04 | 4.00 | 4.54 | 4.084E−04 | 2.674E−05 | 1.00 |
| 5.0 | 1.52 | −45.5 | 202.55 | 0.51 | 4.00 | 1074.25 | 6.515E−04 | 5.600E−05 | 0.25 |
| 9.0 | 1.52 | −45.5 | 37.58 | 0.53 | 4.00 | 80.31 | 5.892E−04 | 2.556E−05 | 1.00 |
| 14.0 | 1.52 | −19.5 | 41.30 | 0.60 | 4.00 | 104.06 | 6.101E−04 | 2.320E−05 | 2.00 |
| 30.0 | 1.52 | −11.1 | 13.54 | 0.92 | 3.00 | 8.58 | 4.841E−04 | 5.785E−05 | 1.00 |
| 36.0 | 1.52 | −11.1 | 9.28 | 1.10 | 3.00 | 2.54 | 3.078E−04 | 6.094E−05 | 2.00 |
| 5.0 | 1.55 | −45.5 | 468.84 | 0.50 | 4.00 | −1857.84 | 5.743E−04 | 3.939E−05 | 0.25 |
| 9.0 | 1.55 | −45.5 | 49.51 | 0.50 | 4.00 | 78.90 | 5.045E−04 | 3.509E−05 | 1.00 |
| 14.0 | 1.55 | −19.5 | 70.45 | 0.57 | 4.00 | 43.96 | 5.539E−04 | 3.798E−05 | 2.00 |
| 30.0 | 1.55 | −11.1 | 19.87 | 0.88 | 2.00 | 20.06 | 7.638E−04 | 5.259E−05 | 1.00 |
| 36.0 | 1.55 | −11.1 | 12.86 | 1.00 | 2.00 | 4.28 | 5.142E−04 | 6.986E−05 | 2.00 |

| Refractive power/D | Transition zone | | | | Aberration correction zone | | | |
|---|---|---|---|---|---|---|---|---|
| | Qa | Ra2 | $A_{4a}$ | $A_{6a}$ | Qa | Ra3 | $A_{4a}$ | $A_{6a}$ |
| 5.0 | −243.04 | 30.90 | −1.326E−03 | 2.345E−05 | 121.96 | 51.50 | −1.140E−04 | −2.509E−06 |
| 9.0 | −12.12 | 17.60 | −1.332E−04 | 6.697E−08 | −2.57 | 19.20 | −3.783E−05 | 8.313E−08 |
| 14.0 | −3.32 | 14.87 | −8.528E−05 | 2.586E−07 | −1.89 | 15.57 | −5.345E−05 | 1.344E−07 |
| 30.0 | −0.66 | 5.21 | −1.410E−03 | 1.710E−05 | −0.06 | 5.80 | −1.029E−03 | −2.482E−06 |
| 5.0 | −253.83 | 10.00 | −6.020E−04 | 7.375E−06 | −166.20 | 25.40 | −5.537E−04 | 7.046E−06 |
| 9.0 | −40.50 | 16.00 | −4.609E−04 | 5.661E−06 | −8.03 | 35.65 | −1.848E−05 | 8.705E−09 |
| 14.0 | −33.86 | 20.75 | −1.454E−04 | 5.749E−07 | 19.70 | 40.00 | −7.569E−05 | −2.009E−07 |
| 30.0 | −7.19 | 10.72 | −3.862E−04 | 3.959E−06 | −1.18 | 13.00 | −1.947E−04 | 2.402E−07 |
| 36.0 | −1.60 | 8.22 | −3.518E−04 | 2.234E−06 | −0.76 | 9.09 | −2.353E−04 | −6.651E−08 |
| 5.0 | −493.00 | 8.00 | −4.734E−04 | 4.720E−06 | −207.55 | 34.50 | −5.712E−04 | 8.855E−06 |
| 9.0 | −137.31 | 15.70 | −1.568E−04 | 3.079E−07 | 24.41 | 47.00 | −5.077E−05 | −9.746E−08 |
| 14.0 | −29.37 | 30.55 | −2.574E−04 | 1.842E−06 | 190.07 | 68.70 | −1.503E−04 | −1.102E−06 |
| 30.0 | −7.07 | 17.38 | −4.715E−04 | 5.058E−06 | 6.42 | 19.65 | −2.819E−04 | −1.555E−06 |
| 36.0 | −2.47 | 12.11 | −1.791E−04 | 2.638E−07 | −1.68 | 12.75 | −1.360E−04 | −1.068E−07 |

TABLE 2.10

Some embodiments of an artificial lens according to the second aspect of the present invention embodied as a phakic intraocular lens

| Refractive power/D | Refractive index | Rp | Focal extension zone | | | | | | Transition zone | |
|---|---|---|---|---|---|---|---|---|---|---|
| | | | Ra1 | CT | Diameter | Qp | $A_{4p}$ | $A_{6p}$ | Width | Q |
| −5 | 1.46 | 24.5 | Infinity | 0.1 | 4.00 | 71.431 | −2.4556E−03 | −3.2775E−04 | 0.25 | 58.40 |
| −20 | 1.46 | 6.2 | Infinity | 0.1 | 3.00 | −9.364 | 2.2734E−03 | −1.8690E−04 | 1.00 | 3.11 |
| −25 | 1.46 | 4.9 | Infinity | 0.1 | 2.00 | 0.199 | 4.3585E−04 | 1.0006E−04 | 2.00 | 0.52 |
| −5 | 1.55 | 42.8 | Infinity | 0.1 | 4.00 | 271.698 | −1.1441E−03 | −1.9348E−04 | 0.25 | 0.34 |
| −20 | 1.55 | 10.7 | Infinity | 0.1 | 3.00 | 14.892 | −1.6115E−03 | −3.8344E−04 | 1.00 | −30.36 |
| −25 | 1.55 | 8.56 | Infinity | 0.1 | 2.00 | −24.260 | 4.4893E−03 | −2.5745E−04 | 2.00 | −0.08 |

| Refractive power/D | Transition zone | | | Aberration correction zone | | | |
|---|---|---|---|---|---|---|---|
| | Ra2 | $A_{4p}$ | $A_{6p}$ | Q | Ra3 | $A_{4p}$ | $A_{6p}$ |
| 5 | 34.0 | −4.0590E−03 | 1.3581E−04 | −4.276 | 43.2 | 1.9447E−04 | 1.1417E−06 |
| 20 | 7.45 | −1.2648E−04 | 4.5699E−05 | −0.941 | 6.30 | 1.0206E−04 | 1.8832E−05 |
| 25 | 4.65 | −5.3567E−04 | −7.3474E−05 | 0.421 | 4.49 | −1.4377E−03 | −8.3885E−05 |
| 5 | 98.5 | 8.1239E−04 | 1.5222E−04 | −1125 | 75.8 | 1.6215E−03 | −3.6690E−05 |
| 20 | 11.1 | 1.9166E−03 | −1.1116E−04 | −30.45 | 14.0 | 2.2157E−03 | −1.1667E−04 |
| 25 | 8.50 | −2.0064E−05 | −2.0064E−05 | −0.672 | 8.35 | −1.9829E−04 | 9.0019E−08 |

TABLE 2.11

Some embodiments of an artificial lens according to the second aspect of the present invention embodied as a contact lens

| Refractive power/D | Refractive index | Rp | Focal extension zone | | | | | | | Transition zone |
| --- | --- | --- | --- | --- | --- | --- | --- | --- | --- | --- |
| | | | Ra1 | Qp | CT | Diameter | Qa | $A_{4a}$ | $A_{6a}$ | Width |
| 10.0D | 1.38 | 8.4 | 6.91 | 0 | 0.15 | 4 | 0.09 | 4.46E−05 | 2.92E−06 | 0.25 |
| 0D | 1.44 | 8.8 | 8.79 | −0.7 | 0.07 | 3.5 | −0.21 | −5.34E−05 | −5.24E−06 | 1 |
| −3.0D | 1.44 | 8.8 | 9.38 | −0.3 | 0.07 | 3 | 0.25 | 5.14E−05 | −6.74E−05 | 1.5 |
| −20.0D | 1.38 | 8.9 | 16.78 | −0.8 | 0.07 | 4 | −1.84 | −3.50E−05 | −3.57E−06 | 2 |

| Refractive power/D | Transition zone | | | | Aberration correction zone | | | |
| --- | --- | --- | --- | --- | --- | --- | --- | --- |
| | Qa | Ra2 | $A_{4a}$ | $A_{6a}$ | Qa | Ra3 | $A_{4a}$ | $A_{6a}$ |
| 10.0D | −1.35 | 6.262 | −9.54E−05 | −9.54E−05 | −0.85 | 6.889 | 8.09E−05 | 4.59E−05 |
| 0D | −0.28 | 8.79 | −6.79E−05 | −6.55E−06 | −0.26 | 8.79 | −6.34E−05 | −6.15E−06 |
| −3.0D | −0.27 | 9.25 | −4.71E−05 | −3.80E−06 | −0.07 | 9.38 | −1.30E−05 | −1.37E−06 |
| −20.0D | −1.38 | 16.79 | −3.83E−05 | −2.41E−06 | −0.39 | 16.77 | 3.89E−06 | 1.48E−07 |

The concept of using an aspherical surface to achieve focal extension according to the second aspect of the present invention may be applied to various optical products including, but not limited to, monofocal artificial lenses, diffractive multifocal artificial lenses, refractive multifocal artificial lenses, toric artificial lenses, etc.

The second aspect of the present invention has the following effects (explained by taking an aphakic intraocular lens as an example).

Figure 27:
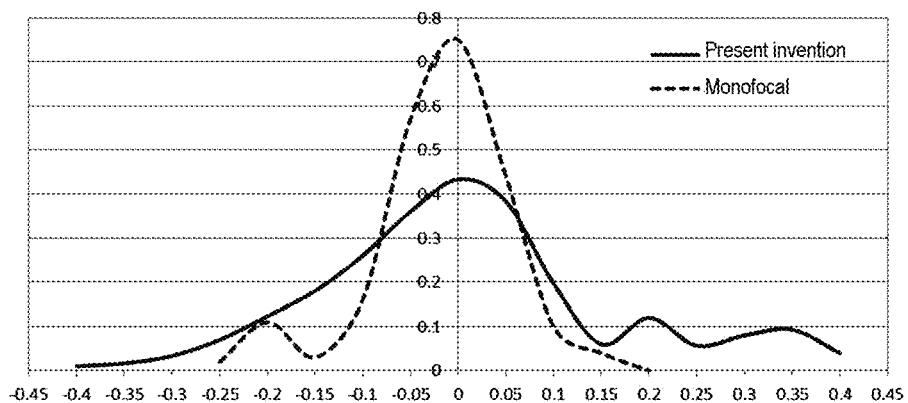
FIG. 27 illustrates the through focus response curves for the aphakic intraocular lens of the second aspect of the present invention and the prior art monofocal intraocular lens, with focal point extension of ≤0.5D.

(1) Providing a Defocal Amount Higher than that of the Prior Art Monofocal Artificial Lens and Realizing Focal Extension In the prior art aspherical artificial lens, the surface shape has slight and gradual change from the center to the periphery and the amount of change is larger at the periphery. The difference in the surface shape is almost negligible within a small aperture, such as 3 mm. The prior art aspherical intraocular lens also has a small variation in refractive power with aperture. For prior art aspherical intraocular lenses of 20D, the intraocular lenses with spherical aberration of 0, 0.18 μm, 0.20 μm and 0.27 μm have a difference in refractive power ΔD at r=1.5 mm and r=1.0 mm of about 0D, −0.33D, −0.35D and −0.45D, respectively, with the refractive power gradually decreased as the aperture increases. In contrast, the absolute value of the difference in refractive power |ΔD| of the aphakic intraocular lens according to the second aspect of the present invention at r=1.5 mm and r=1.0 mm is greater than or equal to 0.50D. The refractive power of the cornea is gradually increased as the aperture increases. In order to make the refractive power of the whole eye consistent and to achieve higher resolution, the refractive power of the prior art aspherical artificial lens decreases as the aperture increases. The refractive power of the aphakic intraocular lens according to the second aspect of the present invention is not limited to increase or decrease as the aperture increases, but the key point is the amount of change of the refractive power with the aperture. It is intended to realize a relatively large defocal change under the condition of the size of pupil of the human eye (about 3 mm pupil) in a normal environment, without affecting the resolution of the human eye, so as to realize focal extension. The focal extension effect can be seen in a through focus response curve shown in FIG. 27.

Figure 28:
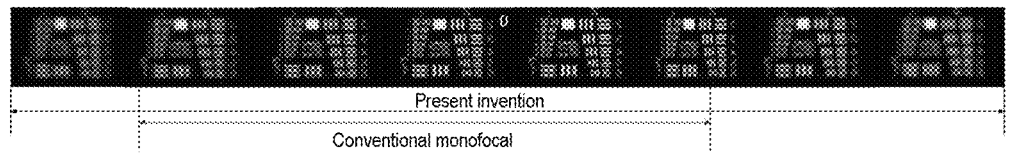
FIG. 28 shows an embodiment of the second aspect of the present invention, which allows for an extended depth of field of the human eye without affecting far focal point vision and without any glare.

Under the concept of the second aspect of the present invention, an aphakic intraocular lens may provide the human eye with a focal extension of greater than or equal to 0.5D. The human eye has a depth of field of about +1.0D. In conjunction with the depth of field of the human eye, the aphakic intraocular lens according to the second aspect of the present invention, after being implanted, can provide a visual distance of greater than or equal to 1.5D for the human eye, and the vision is clear in the whole range. FIG. 28 shows a whole-range USAF optotype of the aphakic intraocular lens according to the second aspect of the present invention. It can be seen that the imaging quality at two end points is at the same level with that of far and near focal points of the prior art multifocal lens, and the definition within the two end points is close to that of the monofocal intraocular lens. With respect to resolution, it is not very different from a monofocal intraocular lens.

(2) Providing Clear and Non-Glare Far Vision

In all existing solutions of aphakic intraocular lens for realizing mid-range vision and near vision, the far vision is greatly influenced. Because of influences light splitting, focal point interference and the like, glare occurs, affecting the postoperative visual effect. The embodiments of the second aspect of the present invention make use of the excessive resolution of the artificial lens eye to achieve mid-range vision without affecting the imaging quality of the far focal point and without any glare interference.

Figure 29:
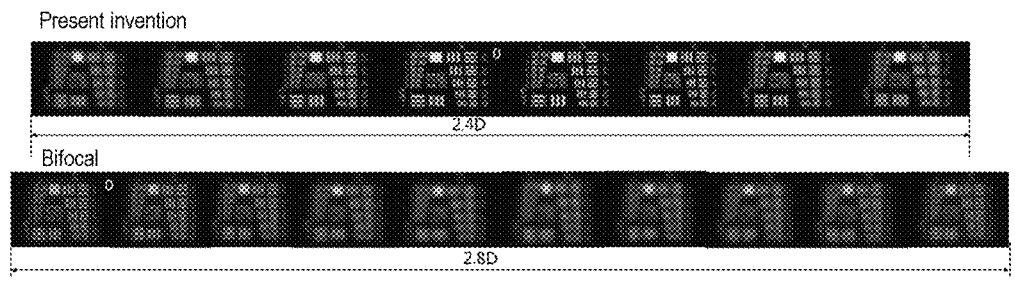
FIG. 29 shows the imaging quality of an embodiment of the second aspect of the present invention in comparison to a prior art bifocal intraocular lens.

FIG. 29 is a graph showing the image qualities of an aphakic intraocular lens of the second aspect of the present invention and a prior art multifocal intraocular lens (with additional refractive power+2.8D) measured with the same light intensity. The imaging quality of the aphakic intraocular lens of the second aspect of the present invention shows good resolution in the full range, and no glare interference exists at the optimal resolution, and although the definition at the two ends is reduced, no halo phenomenon occurs which generally exists in the multifocal intraocular lens. Moreover, the imaging of the aphakic intraocular lens of the second aspect of the present invention is continuous with no breakpoint.

(3) Without Pupil Dependence

The optical zone of the aspherical surface of the second aspect of the present invention is distributed within the range of the pupil of conventional size. When the pupil of the human eye has a conventional size (about 2.5-3.0 mm in diameter), defocus caused by the refractive power of aspherical surface provides the human eye with adequate depth of focus and mid-range vision. When the pupil of the human eye is small (such as under strong light or being a small pupil, the diameter of the pupil is less than or equal to 1.5 mm), although the depth of field added by the aphakic intraocular lens according to the second aspect of the present invention is limited, the depth of field of the human eye itself is increased, and the human eye can still obtain good mid-range vision.

The above advantageous effects can also be found in the phakic intraocular lenses and the contact lenses worn outside the human eye.

While the present invention has been described with reference to exemplary embodiment(s), it will be understood by those skilled in the art that the present invention is not limited to the precise construction and components described herein and that various modifications, changes and variations may be apparent from the foregoing descriptions without departing from the spirit and scope of the present invention as defined in the appended claims. The present invention is not limited by the illustrated ordering of steps, as some steps may occur in different orders and/or concurrently with other steps. Therefore, the present invention is not limited to the particular embodiment(s) as disclosed, but will include all embodiments falling within the scope of the appended claims.

The invention claimed is:

1. An artificial lens having an optical portion comprising a focal extension zone at the center, an anterior surface and/or a posterior surface of the focal extension zone being an aspherical surface, an expression of a curve of the aspherical surface on a plane rZ of the two-dimensional coordinate system is as follows:

$$z(r) = \frac{\frac{1}{R} * r^2}{1 + \left(1 - (1+Q) * \left(\frac{1}{R}\right)^2 * r^2\right)^{\frac{1}{2}}} + \sum_{i=m}^{n} A_{2i} * r^{2i}$$

wherein R is the radius of curvature of the basal spherical surface of the aspherical surface, r is the perpendicular distance from a point on the curve to the abscissa axis (Z), $A_{2i}$ is aspherical high-order term coefficient, m and n are both integers not less than 1 and n>m, Q is aspherical coefficient, wherein points on the aspherical surface are obtained in a way that the curve rotates about the abscissa axis (Z) for symmetry variation, wherein an absolute value of a difference in refractive power |ΔD| of the artificial lens at r=1.5 mm and r=1.0 mm is greater than or equal to 0.50D.

2. The artificial lens according to claim 1, wherein the difference in refractive power ΔD of the artificial lens at r=1.5 mm and r=1.0 mm is greater than or equal to 0.50D.

3. The artificial lens according to claim 1, wherein the artificial lens has an MTF of 0 to 0.42, or 0.13 to 0.37, or 0.13 to 0.28 at a spatial frequency of 100 lp/mm and at a 3 mm aperture in a human eye model.

4. The artificial lens according to claim 1, wherein the artificial lens is embodied as an aphakic intraocular lens for replacing a natural lens of a cataract patient.

5. The artificial lens according to claim 4, wherein an absolute value of the difference in refractive power |ΔD| of the aphakic intraocular lens at r=1.5 mm and r=1.0 mm is 0.60D to 2.70D, or 1.00D to 2.70D.

6. The artificial lens according to claim 4, wherein an asphericity of the aphakic intraocular lens is characterized by a difference in height of the aspherical surface at r=1.5 mm and r=1.0 mm, namely:

$$\Delta Z = Z(r=1.5) - Z(r=1.0)$$

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the aphakic intraocular lens at r=1.5 mm and r=1.0 mm is 0.002 to 0.138 mm, or 0.003 to 0.138 mm, or 0.004 to 0.138 mm.

7. The artificial lens according to claim 4, wherein the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.44 to 10.00, or 0.46 to 10.00, or 0.44 to 0.99, or 0.46 to 0.99.

8. The artificial lens according to claim 4, wherein the aphakic intraocular lens has an optical portion with an anterior surface and a posterior surface, one of the anterior surface and the posterior surface comprising an aspherical surface and the other of the anterior surface and the posterior surface comprising a multifocal structure that provides the aphakic intraocular lens with two or more focal points, such that a through focus response curve of the aphakic intraocular lens at a spatial frequency of 50 lp/mm and at a 3 mm aperture has two or more peaks, wherein at least one pair of adjacent peaks of the two or more peaks corresponds to a difference in refractive power which has an absolute value greater than or equal to 1.6D and a minimum value of MTF between the at least one pair of adjacent peaks is greater than or equal to 0.05.

9. The artificial lens according to claim 8,
wherein the aspherical surface is defined by a scale factor η which is a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface at r=1.5 mm and r=1.0 mm is 1.02 to 1.93, or 1.04 to 1.86, or 1.06 to 1.86.

10. The artificial lens according to claim 8, wherein the at least one pair of adjacent peaks of the through focus response curve of the aphakic intraocular lens at a spatial frequency of 50 lp/mm and at a 3 mm aperture corresponds to a difference in refractive power which has an absolute value of 1.6D to 2.8D, or 2.0D to 2.5D, or 2.2D to 2.5D, or 2.4 to 2.5D.

11. The artificial lens according to claim 8, wherein the aspherical surface is located centrally within 5 mm, or within 4 mm, or within 3 mm in diameter of the optical portion of the aphakic intraocular lens.

12. The artificial lens according to claim 8, wherein the aphakic intraocular lens has 2 or 3 focal points.

13. The artificial lens according to claim 8, wherein the multifocal structure comprises a plurality of diffractive rings, wherein the diffractive ring closest to the centre of the optical portion has a radius of 0.59 to 0.80 mm, or 0.63 to 0.72 mm, or 0.63 to 0.68 mm, or 0.63 to 0.64 mm.

14. The artificial lens according to claim 13, wherein the number of diffractive rings of the intraocular lens within 3 mm in diameter of the optical portion is 3 to 7, or 4 to 5, or 5.

15. The artificial lens according to claim 13, wherein the height of the diffractive rings is 1.02 to 2.66 μm.

16. The artificial lens according to claim 1, wherein the artificial lens is embodied as a phakic intraocular lens implanted into a phakic eye for refractive correction.

17. The artificial lens according to claim 16, wherein an absolute value of the difference in refractive power |ΔD| of the phakic intraocular lens at r=1.5 mm and r=1.0 mm is 0.50D to 4.04D, or 0.84D to 4.04D.

18. The artificial lens according to claim 16, wherein an asphericity of the phakic intraocular lens is characterized by a difference in height of the aspherical surface at r=1.5 mm and r=1.0 mm, namely:

$$\Delta Z = Z(r=1.5) - Z(r=1.0)$$

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the phakic intraocular lens at r=1.5 mm and r=1.0 mm is 0.009-0.146 mm.

19. The artificial lens according to claim 16, wherein the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.74 to 1.23, or 1.01 to 1.23.

20. The artificial lens according to claim 1, wherein the artificial lens is embodied as a contact lens worn outside the human eye.

21. The artificial lens according to claim 20, wherein an absolute value of the difference in refractive power |ΔD| of the contact lens at r=1.5 mm and r=1.0 mm is 0.50D to 1.515D, or 0.627D to 1.515D.

22. The artificial lens according to claim 20, wherein an asphericity of the contact lens is characterized by a difference in height of the aspherical surface at r=1.5 mm and r=1.0 mm, namely:

$$\Delta Z = Z(r=1.5) - Z(r=1.0)$$

wherein ΔZ is the difference in height of the aspherical surface, Z(r=1.5) is a height of the aspherical surface at a perpendicular distance of 1.5 mm from the abscissa axis (Z); Z(r=1.0) is a height of the aspherical surface at a perpendicular distance of 1.0 mm from the abscissa axis (Z), wherein the difference in height ΔZ of the aspherical surface of the contact lens at r=1.5 mm and r=1.0 mm is 0.0389 to 0.0946 mm, or 0.0431 to 0.0946 mm.

23. The artificial lens according to claim 20, wherein the aspherical surface is defined by a scale factor η of equivalent radius of curvature, the scale factor η being a ratio of the equivalent radii of curvature $\overline{R}$ of the aspherical surface at different positions of the curve on the plane rZ of the two-dimensional coordinate system, wherein the equivalent radius of curvature $\overline{R}$ is expressed as:

$$\overline{R} = \frac{r^2 + z^2}{2 \cdot z}$$

wherein r is the perpendicular distance from a point on the curve to the abscissa axis (Z), i.e. the height difference between the point and the vertex of the aspherical surface, z is the perpendicular distance from the point on the curve to the ordinate axis (r), wherein the scale factor η of the aspherical surface of the aphakic intraocular lens at r=1.5 mm and r=1.0 mm is 0.978 to 1.026, or 0.978 to 0.99.

24. The artificial lens according to claim 1, wherein the focal extension zone is spanned within a diameter of less than or equal to 4.0 mm, or within a diameter of less than or equal to 3.5 mm, or within a diameter of less than 3.0 mm.

25. The artificial lens according to claim 1, wherein the optical portion of the artificial lens further comprises an annular transition zone outside the focal extension zone and an annular aberration correction zone outside the transition zone, wherein the aberration correction zone serves for aberration modification and correction and the transition zone provides a smooth transition in refractive power of the artificial lens.

26. The artificial lens according to claim 25, wherein the transition zone has a width greater than or equal to 0.25 mm, or 0.25 to 2.0 mm, or 0.25 to 1.0 mm.

27. The artificial lens according to claim 25, wherein the transition zone is a combination of a plurality of annular regions.

* * * * *